US008287532B2

(12) United States Patent
Carroll et al.

(10) Patent No.: US 8,287,532 B2
(45) Date of Patent: Oct. 16, 2012

(54) EPICARDIAL MAPPING AND ABLATION CATHETER

(75) Inventors: Sean Carroll, Rancho Cucamonga, CA (US); Jennifer Maffre, Pasadena, CA (US); Maribeth Esguerra, Carson, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 586 days.

(21) Appl. No.: 12/384,992

(22) Filed: Apr. 13, 2009

(65) Prior Publication Data
US 2012/0130366 A1    May 24, 2012

(51) Int. Cl.
*A61B 18/18* (2006.01)
(52) U.S. Cl. .......................................... 606/41
(58) Field of Classification Search ............... 604/95.01; 606/38, 39, 41, 46, 47, 48–50; 607/101–102, 607/122, 123; 600/374, 381
See application file for complete search history.

(56) References Cited

U.S. PATENT DOCUMENTS

| | | | |
|---|---|---|---|
| 4,898,591 A | 2/1990 | Jang et al. | |
| 5,104,393 A | 4/1992 | Isner et al. | |
| 5,454,787 A * | 10/1995 | Lundquist | 604/95.01 |
| 5,482,037 A | 1/1996 | Borghi | |
| 5,487,385 A | 1/1996 | Avitall | |
| 5,575,766 A | 11/1996 | Swartz et al. | |
| 5,582,609 A | 12/1996 | Swanson et al. | |
| 5,617,854 A | 4/1997 | Munsif | |
| 5,730,704 A | 3/1998 | Avitall | |
| 5,738,683 A | 4/1998 | Osypka | |
| 5,964,757 A | 10/1999 | Ponzi | |
| 5,997,536 A | 12/1999 | Osswald et al. | |

(Continued)

FOREIGN PATENT DOCUMENTS

EP    1 690 510 A1    8/2006

(Continued)

OTHER PUBLICATIONS

European Search Report for EP 10 25 0703.5, dated Jul. 26, 2010, 8 pages.

*Primary Examiner* — Manuel Mendez
(74) *Attorney, Agent, or Firm* — Christie, Parker & Hale, LLP

(57) ABSTRACT

A catheter adapted for mapping and ablating epicardial tissue from the pericardial cavity includes a catheter body and an electrode assembly that has a tip section and a loop member lying generally within a plane, wherein the tip section includes an ablation electrode exposed on one side of the loop member and an insulation member exposed on an opposite side of the loop member. The catheter also includes a intermediate section between the catheter body and the electrode assembly, wherein the intermediate deflects the loop member and the tip section bi-directionally within the same plane. So arranged, the catheter can be safely maneuvered in the pericardial sac and swept in a side to side motion over the epicardium with the ablation electrode reliably facing and making contact with the epicardium. The tip section can include a balloon that is inflatable to push away surrounding pericardial tissue. The catheter may further include an injection needle whose distal end can extend outside of the tip section to puncture epicardial tissue. A lumen in the injection needle allows for delivery to agents directly to the punctured tissue and thermocouple wires can be carried in the lumen for temperature sensing at the treatment site.

19 Claims, 25 Drawing Sheets

U.S. PATENT DOCUMENTS

| | | | |
|---|---|---|---|
| 6,183,463 B1 * | 2/2001 | Webster, Jr. | 604/528 |
| 6,379,352 B1 | 4/2002 | Reynolds et al. | |
| 6,613,046 B1 | 9/2003 | Jenkins et al. | |
| 6,728,455 B2 | 4/2004 | Kusakari et al. | |
| 6,905,495 B1 | 6/2005 | Fuimaono et al. | |
| 6,939,349 B2 | 9/2005 | Fleischman et al. | |
| 6,973,339 B2 | 12/2005 | Govari | |
| 7,003,342 B2 | 2/2006 | Plaza | |
| 7,063,682 B1 * | 6/2006 | Whayne et al. | 604/95.04 |
| 7,142,903 B2 | 11/2006 | Rodriguez et al. | |
| 7,245,955 B2 | 7/2007 | Rashidi | |
| 7,377,906 B2 | 5/2008 | Selkee | |
| 7,412,273 B2 | 8/2008 | Jais et al. | |
| 7,771,421 B2 * | 8/2010 | Stewart et al. | 606/41 |
| 7,824,403 B2 * | 11/2010 | Vaska et al. | 606/41 |
| 2003/0208195 A1 | 11/2003 | Thompson et al. | |
| 2005/0090818 A1 | 4/2005 | Pike, Jr. et al. | |
| 2006/0106295 A1 | 5/2006 | Jais et al. | |
| 2009/0018497 A1 | 1/2009 | Birchard et al. | |
| 2010/0069834 A1 | 3/2010 | Schultz | |

FOREIGN PATENT DOCUMENTS

| | | |
|---|---|---|
| WO | WO93/20767 | 10/1993 |
| WO | WO98/46149 | 10/1998 |
| WO | WO2008/147961 A1 | 12/2008 |

* cited by examiner

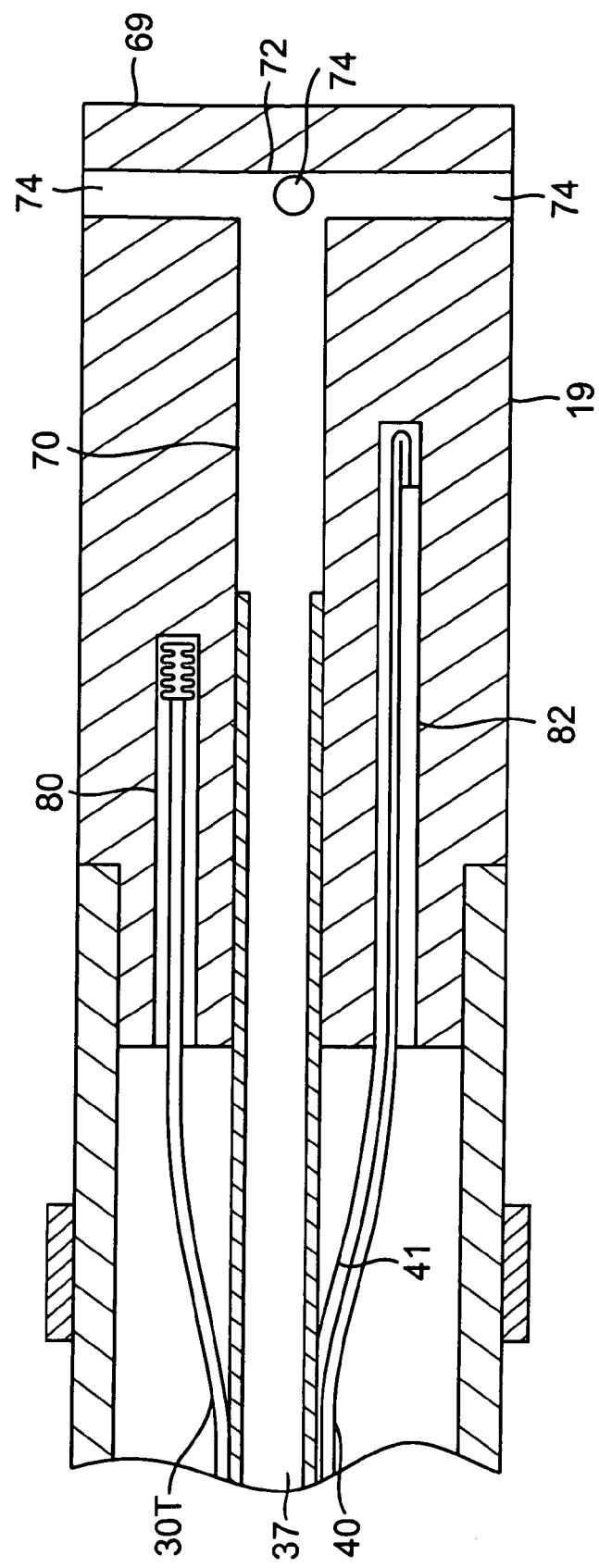

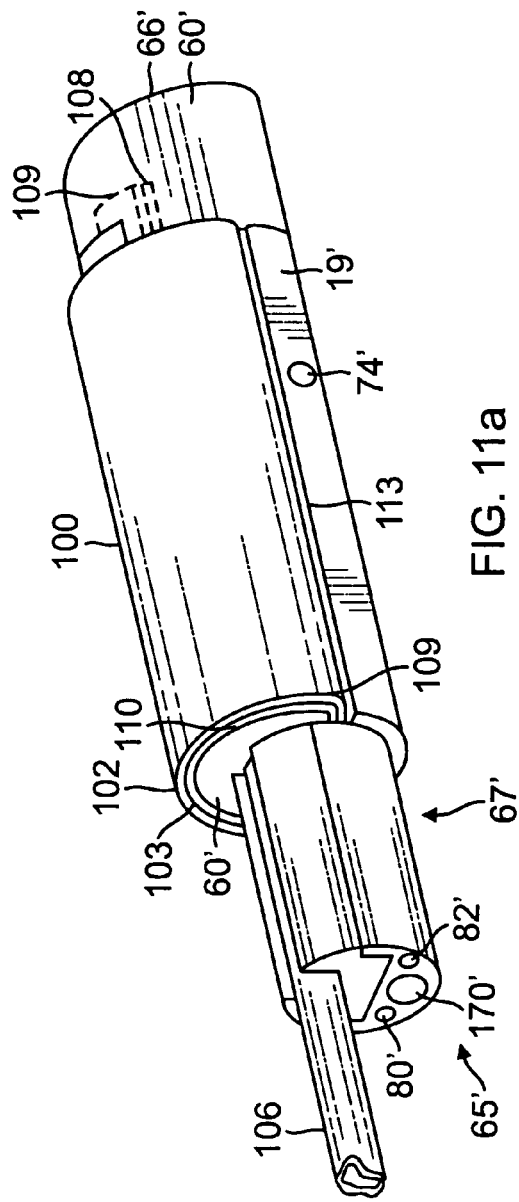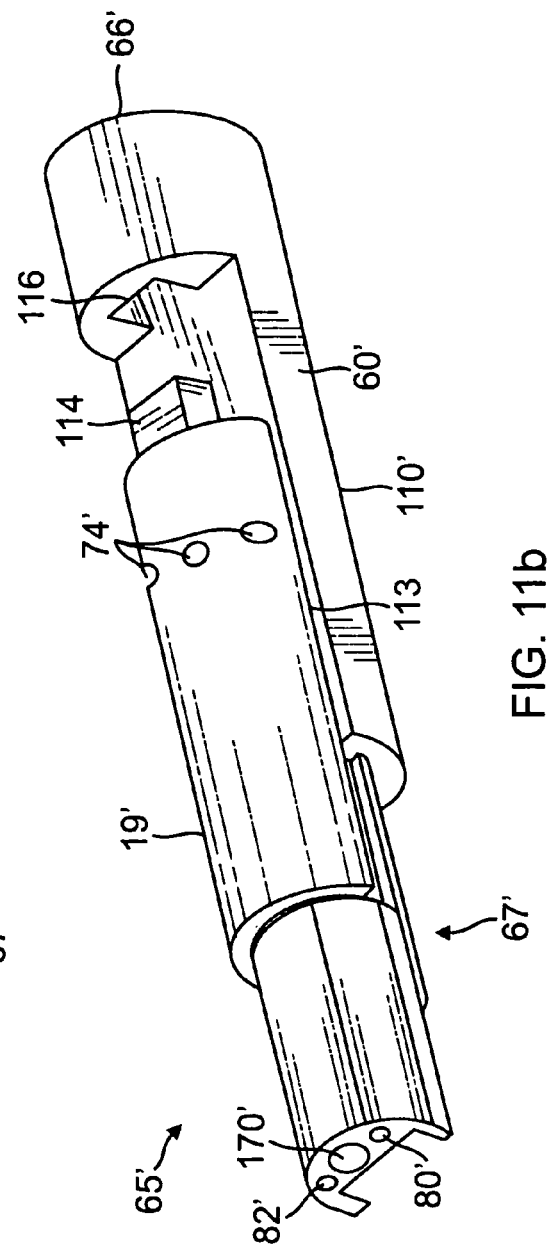
FIG. 11a
FIG. 11b

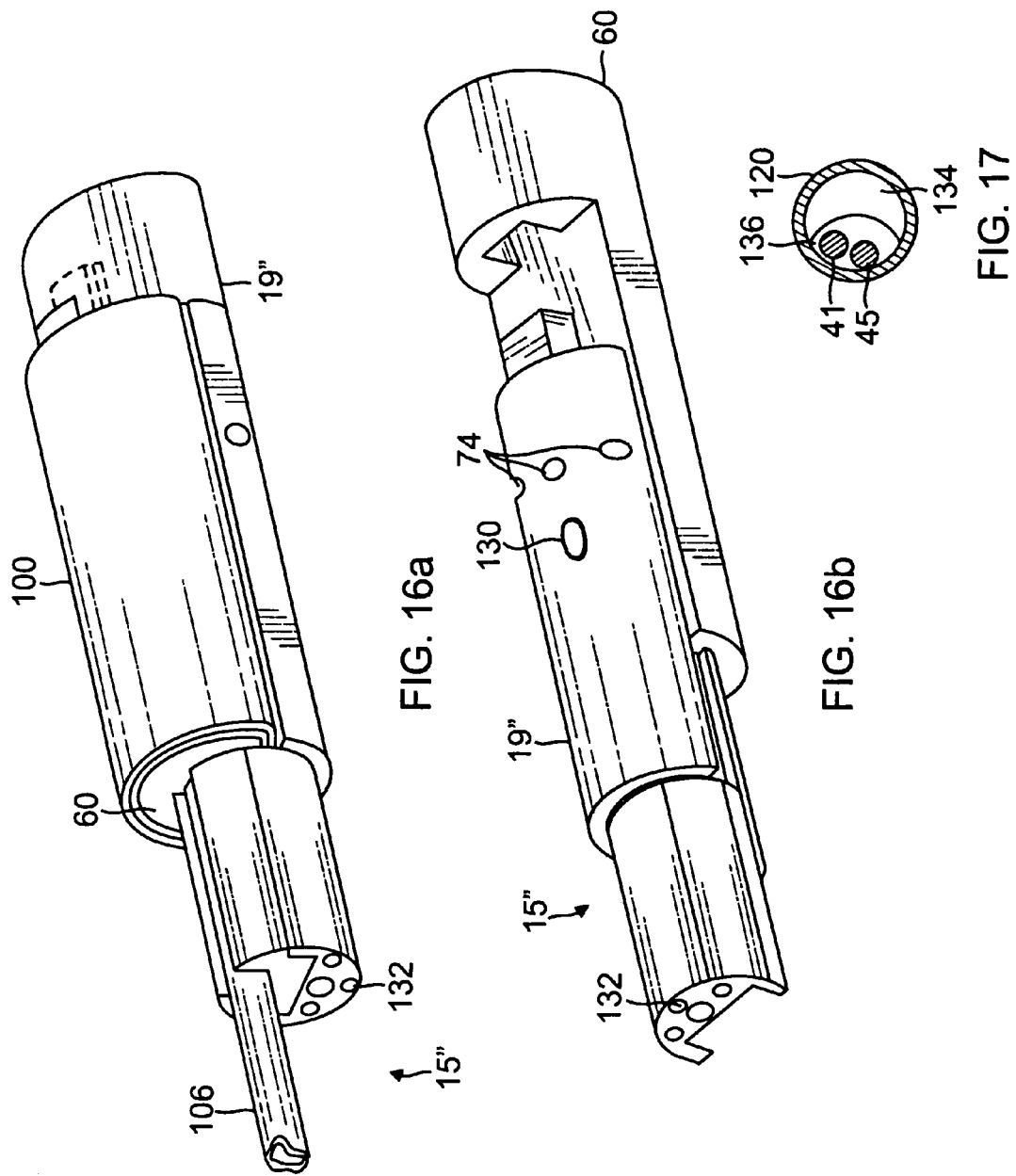

EPICARDIAL MAPPING AND ABLATION CATHETER

FIELD OF INVENTION

The present invention relates to an electrophysiologic catheter that is particularly useful for ablation and sensing electrical activity of epicardial heart tissue.

BACKGROUND OF INVENTION

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Diagnosis and treatment of cardiac arrythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Examples of catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang, et al., U.S. Pat. No. 5,487,385 to Avitall, and U.S. Pat. No. 5,582,609 to Swanson, the disclosures of which are incorporated herein by reference. In addition, various energy delivery modalities have been disclosed for forming such atrial wall lesions, and include use of microwave, laser and more commonly, radiofrequency energies to create conduction blocks along the cardiac tissue wall, as disclosed in WO 93/20767 to Stem, et al., U.S. Pat. No. 5,104,393 to Isner, et al. and U.S. Pat. No. 5,575,766 to Swartz, et al., respectively, the entire disclosures of which are incorporated herein by reference.

In this two-step procedure—mapping followed by ablation—electrical activity at points within the heart is typically sensed and measured by advancing a catheter containing one or more electrical sensors into the heart, and acquiring data at a multiplicity of points. These data are then utilized to select the endocardial target areas at which ablation is to be performed. However, recent techniques have looked to epicardial mapping and ablation to treat ventricular tachycardia. The technique involves introducing a standard ablation catheter into the pericardial space using a subxiphoid pericardial puncture technique.

The parietal pericardium is the outer protective layer or sac that encloses the heart which comprises three layers: epicardium, myocardium and endocardium. A pericardial cavity or space separates the parietal pericardium and the epicardium. A small amount of fluid is secreted by tissues of the parietal pericardium to lubricate surfaces so that heart can move freely inside the parietal pericardium. Clearly, adhesion between the parietal pericardium and the epicardium would interfere with muscular contractions of the heart.

Another potential complication in accessing the epicardium is posed by the phrenic nerve. The phrenic nerve is made up mostly of motor nerve fibers for producing contractions of the diaphragm. In addition, it provides sensory innervation for many components of the mediastinum and pleura, as well as the upper abdomen, especially the liver, and the gall bladder. The right phrenic nerve passes over the right atrium and the left phrenic nerve passes over the left ventricle and pierces the diaphragm separately. Both these nerves supply motor fibers to the diaphragm and sensory fibres to the fibrous pericardium, mediastinal pleura and diaphragmatic peritoneum. Any damage to the phrenic nerve, particularly for senior patients, can cause serious breathing difficulties, especially if the damage is permanent. The lung itself is another organ that is susceptible to damage when ablating the epicardium, although the tissue of the lung can more readily repair itself if burned.

Catheters developed for endocardial uses generally have omnidirectional ablation tips supported on flexible shafts. While such catheters are particularly useful for mapping and ablating in cavities and other tubular regions of or near the heart, the omnidirectional ablation tips when used on the epicardium can significantly increase the risk of harmful and unwanted ablation, such as of the parietal pericardium, the phrenic nerve and/or the lungs. Moreover, the flexible shafts on which such omnidirectional ablation tips are mounted provide no traction or support against a lubricated epicardial surface. The shafts often flip and slide inside the pericardial cavity.

Catheters having lasso assemblies are also known. Such catheters are disclosed in, for example, U.S. Pat. Nos. 6,728, 455, 6,973,339, 7,003,342, 7,142,903, and 7,412,273, the entire disclosures of which are hereby incorporated by reference. "Lasso" catheters are particularly useful for circumferential ablations around the ostium of the pulmonary veins as the "lasso" typically is mounted transversely on the catheter so that the lasso can sit on the ostium. Such an orientation however is not suitable for a relatively narrow and flat space such as the pericardial cavity.

Accordingly, it is desirable that a catheter be adapted for the epicardium such that the ablation tip is directional and that the shaft supports tissue contact at the ablation tip and allows a user more control and predictability in the positioning of the ablation tip. To that end, it is desirable that the shaft be stabilized against the epicardium and deflectable off-plane so that the ablation tip can sweep the surface of the epicardium within the confines of the pericardial space with minimal risk of tissue trauma. It is further desirable that the catheter provides continuous feedback of the potential recordings or electrograms (ECGs) inside during ablation so as to allow a user to know whether the undesired potentials have been successfully blocked by the epicardial ablation.

SUMMARY OF THE INVENTION

The present invention is directed to a catheter adapted for mapping and ablating epicardial tissue from the pericardial sac. In one embodiment, the catheter includes a catheter body, an intermediate section, and an electrode assembly that has a tip section and a loop member lying generally within a plane. The tip section includes an ablation electrode exposed on one side of the loop member to face the epicardium and an insulation member exposed on an opposite side of the loop member to face the pericardium, wherein the intermediate section deflects electrode assembly bi-directionally within a plane. So configured, the catheter can be safely maneuvered in the pericardial sac and swept in a side to side motion over the epicardium with the ablation electrode reliably facing and making contact with the epicardium.

In a detailed embodiment, the loop member is open-ended and has shape memory so that it assumes an atraumatic shape that conforms to the narrow confines of the pericardial cavity but can be straighten when the catheter is inserted into the patient's body. The loop member can also carry ring electrodes suitable for electrophysiologic functions, such as pacing, mapping and sensing.

The intermediate section from which the electrode assembly extends can be preformed with a bend or curvature toward the side of the ablation electrode to further ensure tissue contact at the stabilizing member and the tip section. The intermediate deflectable section may be constructed of a braided and preformed tubing to provide a degree of rigidity to the catheter to facilitate tissue contact.

The tip section can include a balloon that is inflatable to push away surrounding pericardial tissue, including tissue above and to the sides of the tip section. The balloon is fed by an inflation tube that is connected to an inlet port of the balloon that extends into a passage in the tip section.

The catheter can also include an irrigation tubing whose distal end is received in a passage formed in the tip section. Fluid delivered by the irrigation tubing can pass through the passage to cool the tip section and leave the tip section via openings to cool ablated epicardial tissue.

The catheter may further include an injection needle whose distal end can extend outside of the tip section to puncture epicardial tissue. A lumen in the needle allows for delivery of agents directly to the punctured tissue. Thermocouple wires can be carried in the lumen for temperature sensing at the treatment site.

BRIEF DESCRIPTION OF THE DRAWINGS

These and other features and advantages of the present invention will be better understood by reference to the following detailed description when considered in conjunction with the accompanying drawings wherein:

FIG. 8. is a side cross-sectional view of the distal tip of FIG. 7a, taken along d-d.

FIG. 11a is a top perspective view of an alternate embodiment of a distal tip in accordance with a feature of the present invention, having an inflation member.

FIG. 11b is a bottom perspective view of the distal tip of FIG. 11a.

FIG. 16a is a top perspective view of an alternate embodiment of a distal tip in accordance with a feature of the present invention, having an inflation member FIG. 16b is a bottom perspective view of the distal tip of FIG. 16a, having an injection needle opening.

FIG. 17 is a longitudinal cross-sectional view of an embodiment of an injection needle.

FIG. 20 is a side cross-sectional view of a junction of an embodiment of a connective tubing and the distal tip of FIG. 18a.

DETAILED DESCRIPTION OF THE INVENTION

Figure 1:
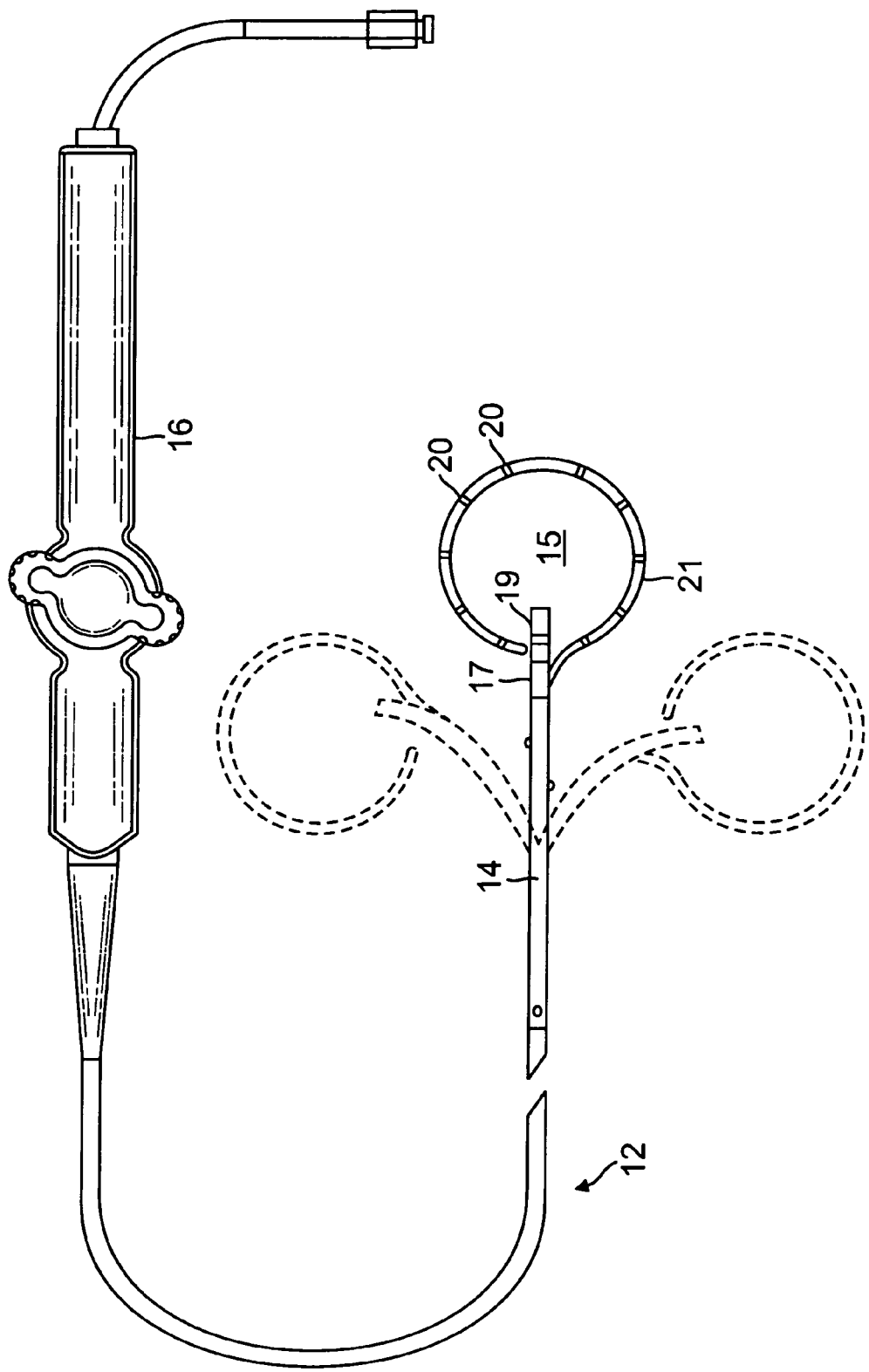
FIG. 1 is a top plan view of an embodiment of a catheter of the present invention.

With reference to FIG. 1, an embodiment of a catheter 10 for epicardial mapping and ablation has an elongated catheter body 12 with proximal and distal ends, an intermediate deflectable section 14 at the distal end of the catheter body 12, and a mapping and ablation electrode assembly 17 distal of the intermediate section. The catheter also includes a control handle 16 at the proximal end of the catheter body 12 for controlling deflection of the intermediate section 14. Advantageously, the electrode assembly 17 has a directional ablation electrode 19 at a distal tip section 15 and a plurality of sensing electrodes 20 mounted on a stabilizing member 21 that facilitates movement and placement of the ablation electrode 19 on an epicardial treatment site.

Figure 2A:
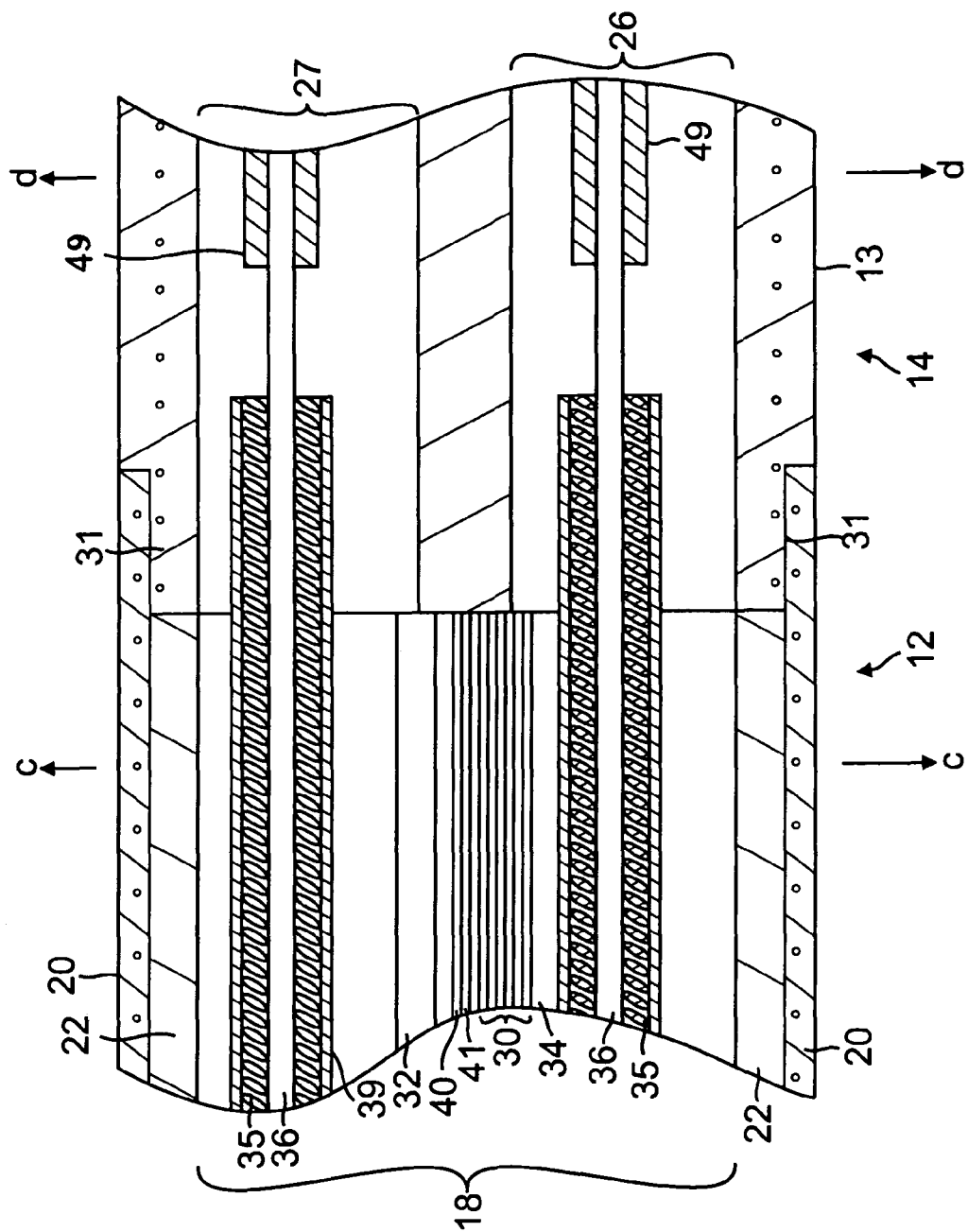
FIG. 2a is a side cross-sectional view of a junction of a catheter body and an intermediate section of the catheter of FIG. 1, taken along a first diameter.
Figure 2B:
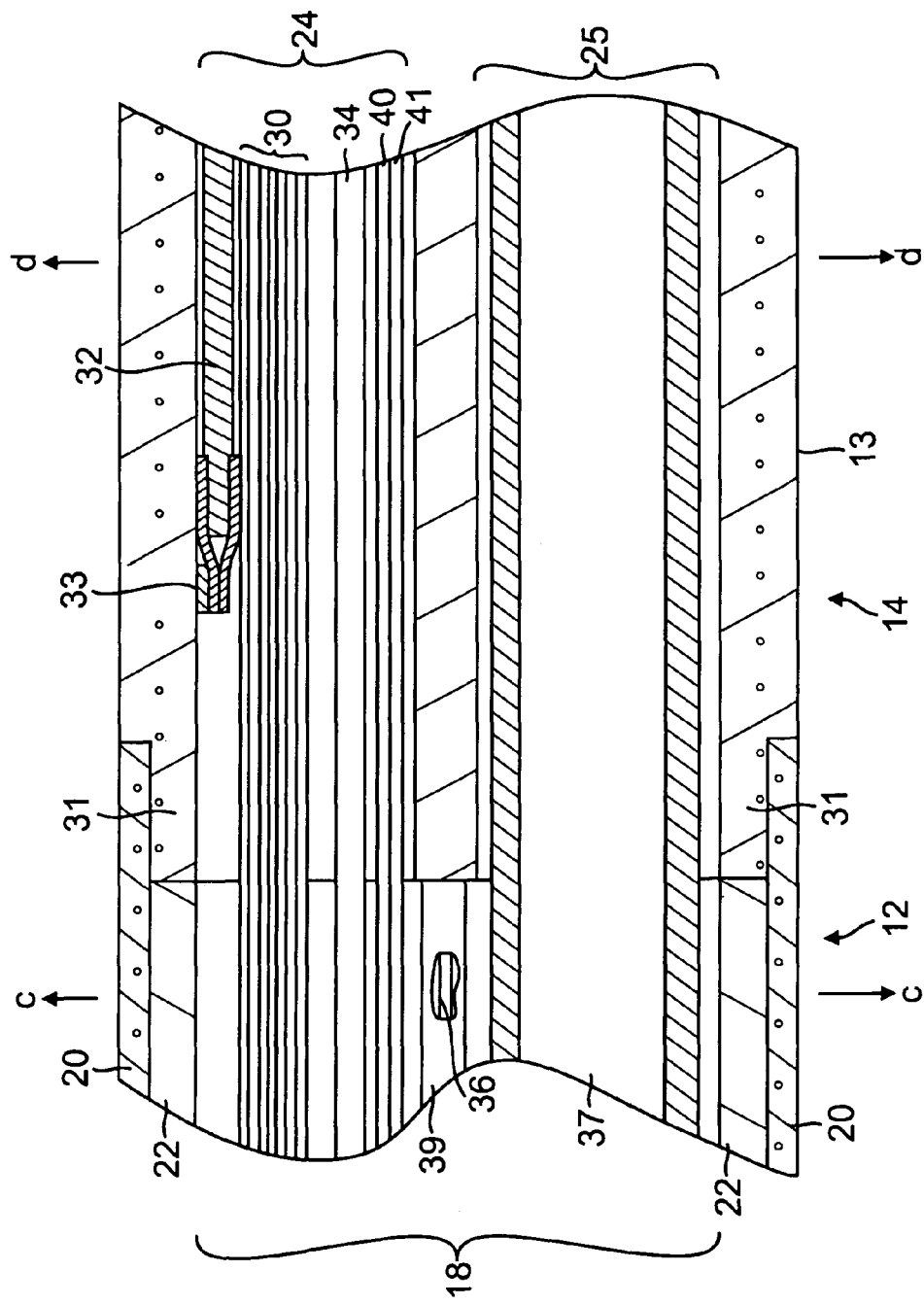
FIG. 2b is a side cross-sectional view of the junction of FIG. 2a, taken along a second diameter generally perpendicular to the first diameter.
Figure 2C:
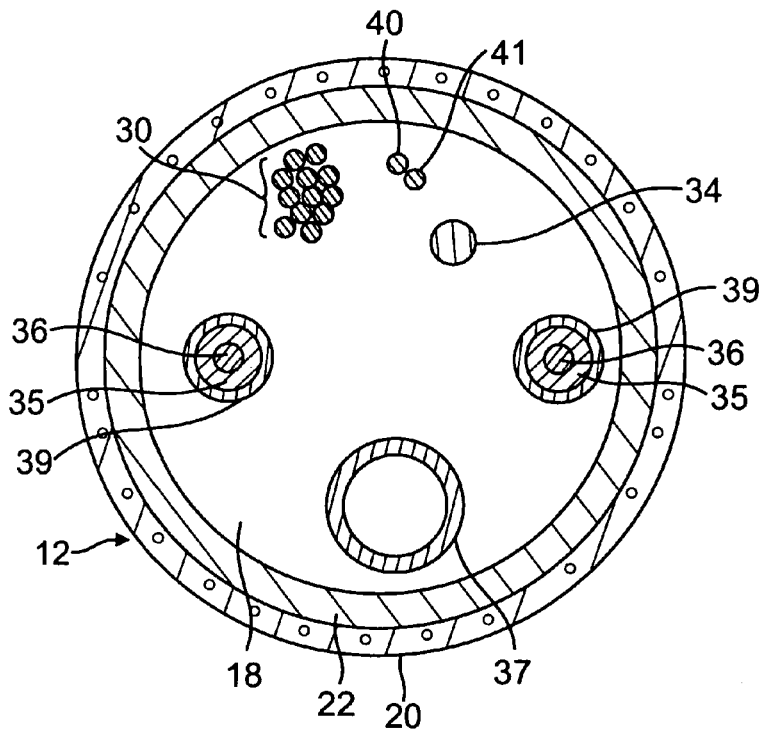
FIG. 2c is a longitudinal cross-sectional view of the catheter body of FIG. 2a, taken along line c-c.

With reference to FIGS. 2a, 2b and 2c, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an embedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller wires, lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch. Glue joints (not shown) are provided to secure the stiffening tube 22 and the outer wall 20 to each other. They may be provided at the proximal and distal ends of the catheter body 12.

Components that extend between the control handle 16 and the deflectable section 14 and/or the tip section 15 pass through the central lumen 18 of the catheter body 12. These include lead wires 30 for each of mapping and ablation electrodes of the electrode assembly 17, an irrigation tubing 37 for delivering fluid to the ablation site from the tip section 15, a cable 34 for an electromagnetic position sensor 75, a pair of puller wires 36 for deflecting the intermediate section 14, and a pair of thermocouple wires 40 and 41 to sense temperature at the tip section 15.

Figure 2D:
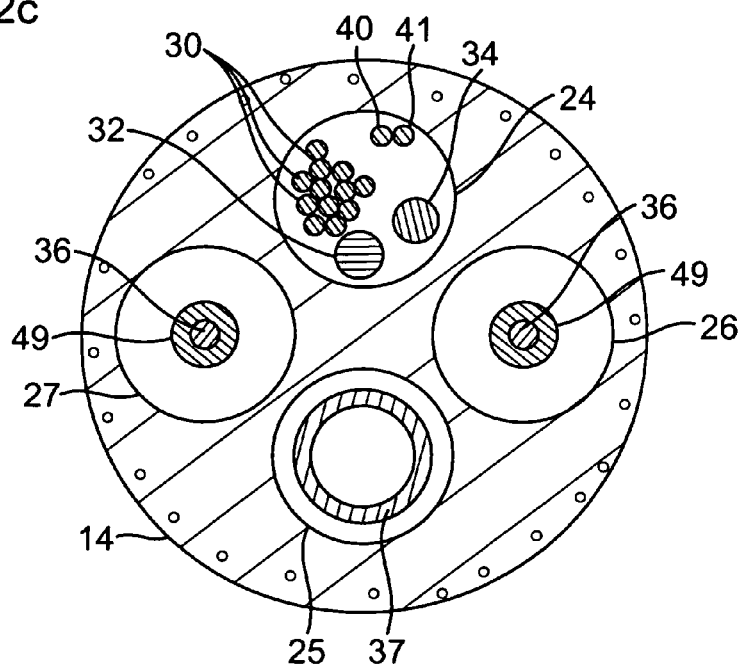
FIG. 2d is a longitudinal cross-sectional view of the intermediate section of FIG. 2a, taking along line d-d.

Illustrated in FIGS. 2a, 2b and 2d is an embodiment of the intermediate section 14 which comprises a short section of tubing 13. The tubing has a braided mesh construction with multiple off-axis lumens, for example lumens 24, 25, 26 and 27. Each of diametrically opposing lumens 26 and 27 carries a respective puller wire 36 to enable bi-directional deflection of the catheter in two opposing directions within a plane (FIG. 1), which movement is well suited for mapping and ablation of epicardial tissue surface within a pericardial cavity. First lumen 24 carries the lead wires 30, the cable 34, the thermocouple wires 40 and 41, as well as a support member 32 with shape-memory for the stabilizing member 21. A distal end of the support member 32 is anchored to a side wall of the tubing 13 as understood by one of ordinary skill in the art, for example, by a T-bar anchor 33. Second lumen 25 carries an irrigation tubing 37.

The tubing 13 of the intermediate section 14 is made of a suitable non-toxic material that is preferably only slightly more flexible than the catheter body 12. A suitable material for the tubing 13 is braided polyurethane, i.e., polyurethane with an embedded mesh of braided stainless steel or the like. The size of each lumen is not critical so long as it is sufficient to house the respective components extending therethrough.

The useful length of the catheter, i.e., the shaft 12 and the section 14 that can be inserted into a patient's body excluding the assembly 17, can vary as desired. In one embodiment, the useful length ranges from about 110 cm to about 120 cm, more preferably about 115 cm to about 117 cm, and still more preferably about 116 cm. The length of the intermediate section 14 is a relatively small portion of the useful length, and preferably ranges from about 6.35 cm to about 7.62 cm, more preferably about 6.43 cm to about 6.5 cm, and still more preferably about 6.4 cm.

A means for attaching the catheter body 12 to the intermediate section 14 is illustrated in FIGS. 2a and 2b. The proximal end of the intermediate section 14 comprises an outer circumferential notch 31 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each of the lumens 26 and 27 of the intermediate shaft 14 carries a puller wire 34 that is preferably coated with Teflon®. The puller wires 36 can be made of any suitable metal, such as stainless steel or Nitinol, or a stronger material such as Vectran® nylon tubing, where the Teflon coating imparts lubricity to the puller wire. The puller wire preferably has a diameter ranging from about 0.006 to about 0.010 inch.

As shown in FIG. 2a, each puller wire 36 passes through a compression coil 35 in surrounding relation to its puller wire 36. The compression coil 35 extends from the proximal end of the catheter body 12 to the proximal end of the intermediate section 14 and may be secured at their proximal and distal ends respectively to the stiffening tube 22 and the proximal end of the intermediate section 14 by glue joints (not shown). The compression coil 35 is made of any suitable metal, preferably stainless steel, and is tightly wound on itself to provide flexibility, i.e., bending, but to resist compression. The inner diameter of the compression coil is preferably slightly larger than the diameter of the puller wire 34. Within the catheter body 12, the outer surface of the compression coil 35 is also covered by a flexible, non-conductive sheath 39, e.g., made of polyimide tubing. The compression coil 35 is anchored at its proximal end to the outer wall 20 of the catheter body 12 by a proximal glue joint and to the intermediate shaft 14 by a distal glue joint. Within the intermediate section 14, each puller wire extends through a protective sheath 49 to prevent the puller wire from cutting into the tubing 13 of the intermediate section 14 during deflection.

Figure 4A:
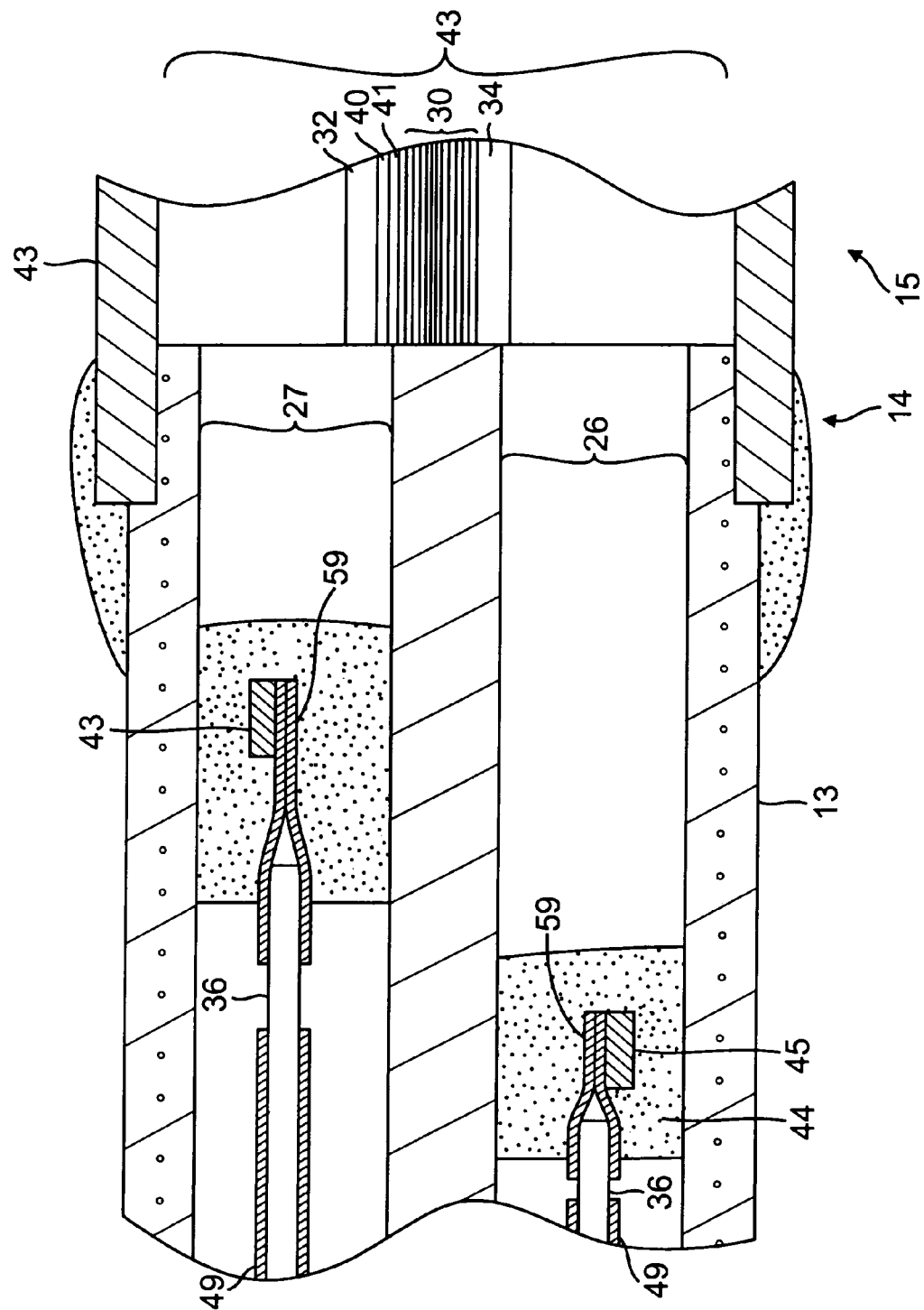
FIG. 4a is a side cross-sectional view of a junction of an intermediate section and a tip section of the catheter of FIG. 1, taken along a first diameter.

Proximal ends of the puller wires 36 are anchored in the control handle 16. Distal ends of the puller wires 36 are anchored near the distal end of the tubing 13 of the intermediate section 14, as illustrated in FIG. 4a. Specifically, a T-shaped anchor is formed, which comprises a short piece of tubular stainless steel 59, e.g., hypodermic stock, which is fitted over the distal end of the puller wire crimped to fixedly secure it to the puller wire. The distal end of the tubular stainless steel 59 is fixedly attached, e.g., by welding, to a cross-piece 45 formed of stainless steel ribbon or the like. The cross-piece 45 extends through a hole (not shown) formed in the tubing 13 and because the cross-piece 45 is larger than the hole and, therefore, cannot be pulled through the hole, the cross-piece 45 anchors the distal end of the puller wire to the distal end of the intermediate section 14. As illustrated, the anchor locations of the distal ends of the puller wires 36 are slightly offset from each other. In areas where the braiding has been removed from the tubing 13, an offset configuration can reduce stresses imposed by the anchor members during deflection. And, depending on locations of the distal and proximal ends of the compression coils, different degrees of deflection are possible, as known in the art. The range of degree of deflection is between about 90 and 180 degrees, preferably between about 90 and 135 degrees, and more preferably between about ±90 degrees.

Figure 3:
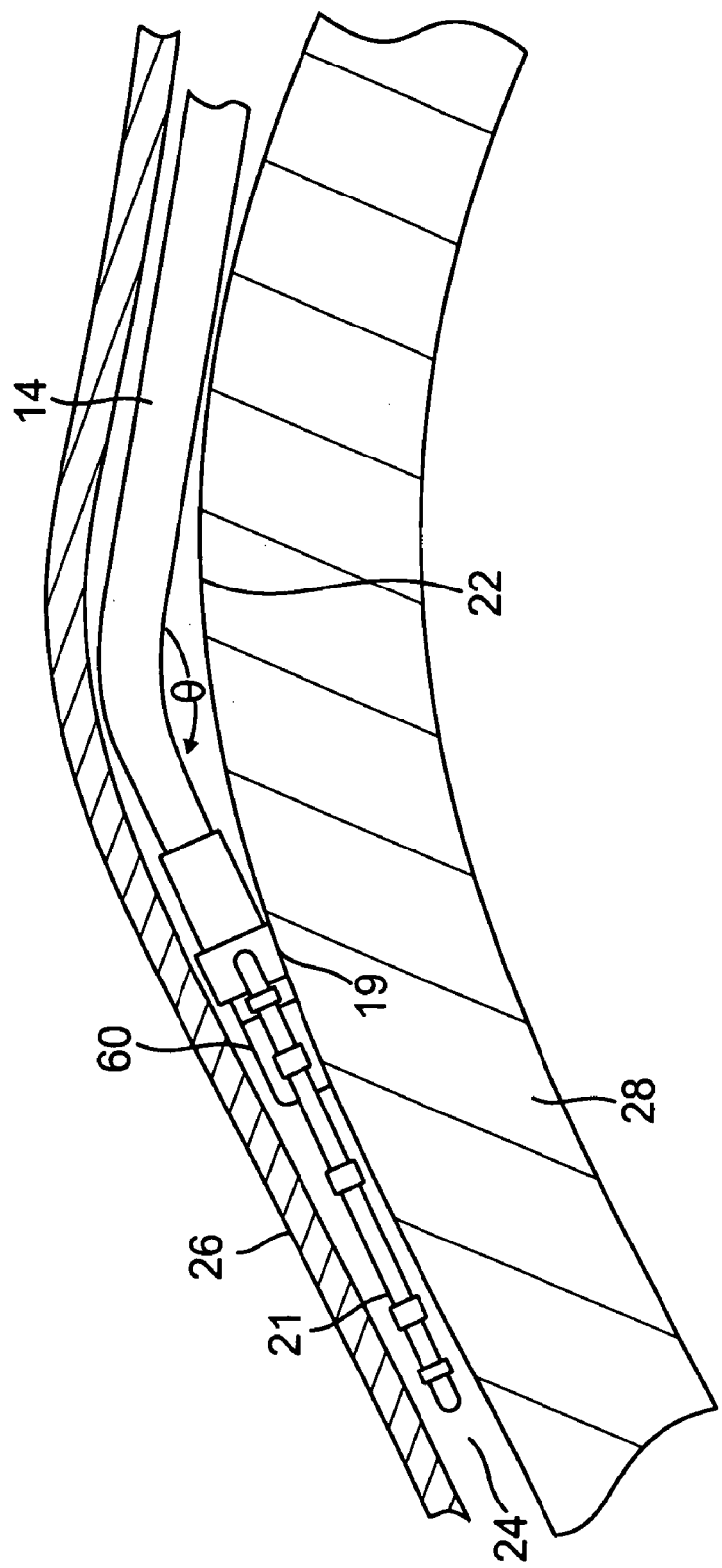
FIG. 3 is a side cross-sectional view of the catheter of FIG. 1 positioned in a pericardial cavity between the parietal pericardium and the epicardium of a heart.

As illustrated in FIG. 3, the deflectable section 14 is advantageously preformed with an angle θ near its distal end at so that the electrode assembly 17 extends at an angle θ from the intermediate deflectable section 14. This angle provides the intermediate deflectable section 14 and tip section 15 with a profile more conforming with the narrow and curved pericardial space 24. This angulation improves tissue contact by the electrode assembly 17 to epicardial surface 22 as the electrode assembly moves from site to site within the pericardial space. The angle θ can range between about 10 and 15 degrees, and more preferably between about 10 and 12 degrees. In accordance with a feature of the present invention, the bi-directional deflection of the electrode assembly 17 combined with the predetermined bend of angle θ in a direction generally perpendicular to the plane of bi-directional deflection enable the electrode assembly 17 to adopt a side-to-side sweeping motion that promotes tissue contact and conformity within the confines of the pericardial space. The angle θ can be formed into the tubing 13 as understood by one of ordinary in the art, including baking the tube in a fixture.

Figure 4B:
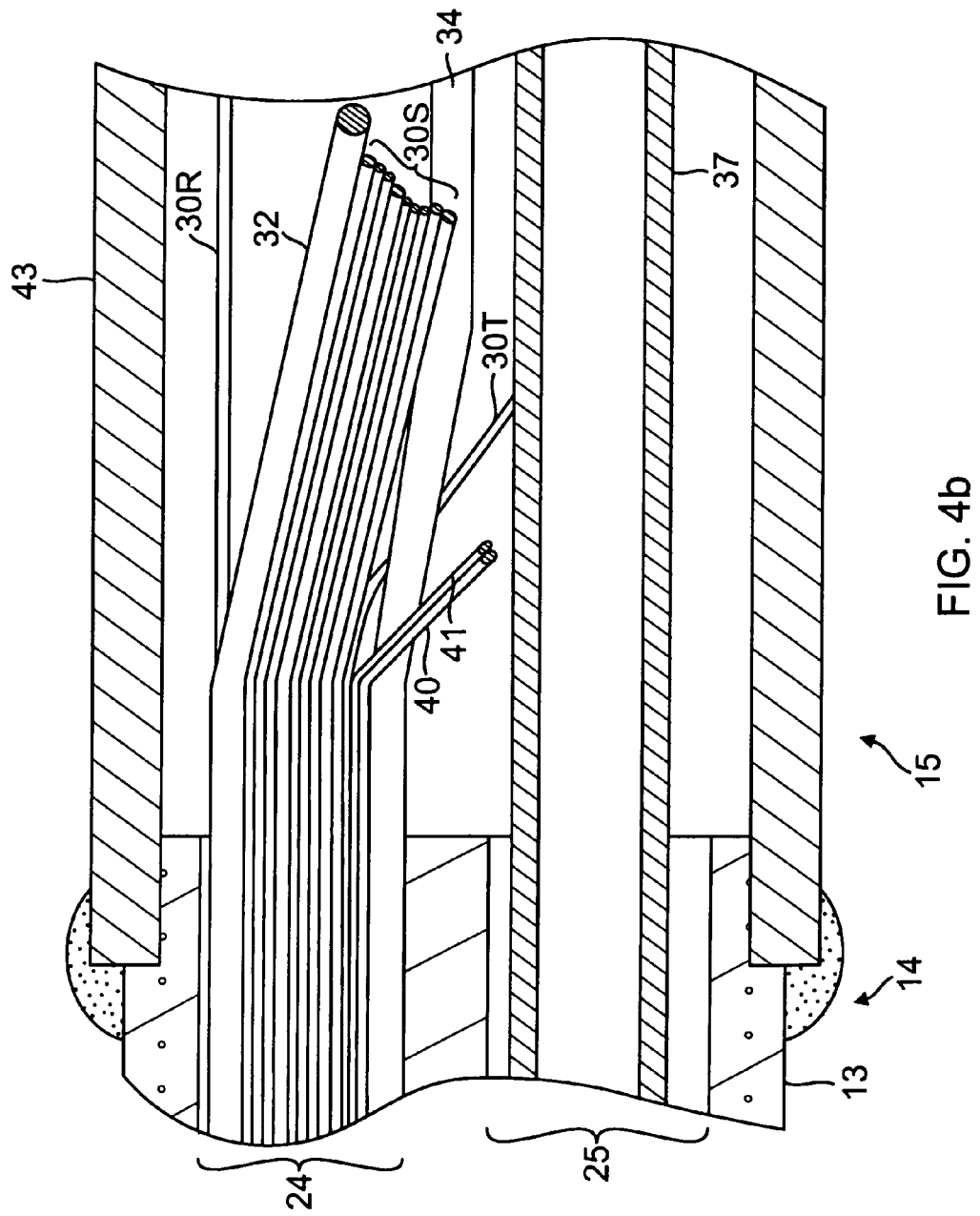
FIG. 4b is a side cross-sectional view of the junction of FIG. 4a, taken along a second diameter generally perpendicular to the first diameter.

At the distal end of the intermediate section 14 is the tip section 15 that is connected by a connective tubing 43. In the illustrated embodiment of FIGS. 4a and 4b, the connective tubing 43 has a single lumen which allows passage of lead wires 30, the support member 32 for the stabilizing member 21, the electromagnetic sensor cable 34 and the irrigation tubing 37. The single lumen of the connective tubing 43 allow these components to reorient themselves from their respective lumens in the intermediate section 14 toward their location within the stabilizing member 21 and the distal tip section 15, as appropriate. As shown, various components criss-cross each other to align themselves properly within the tip section 15.

The electrode assembly 17 includes the distal tip 15 (carrying the directional ablation electrode 19) and the stabilizing member 21 (carrying multiple ring electrodes 20S). There may also be a ring electrode 20R on the connective tubing 43. In accordance with a feature of the present invention, a loop of the stabilizing member 21 spans in two dimensions and lies generally within a plane that also includes the distal tip 15. The entirety of the electrode assembly 17 can be confined within this plane. As shown in FIG. 3, the electrode assembly 17 adopts a generally flat or planar profile.

Figure 5:
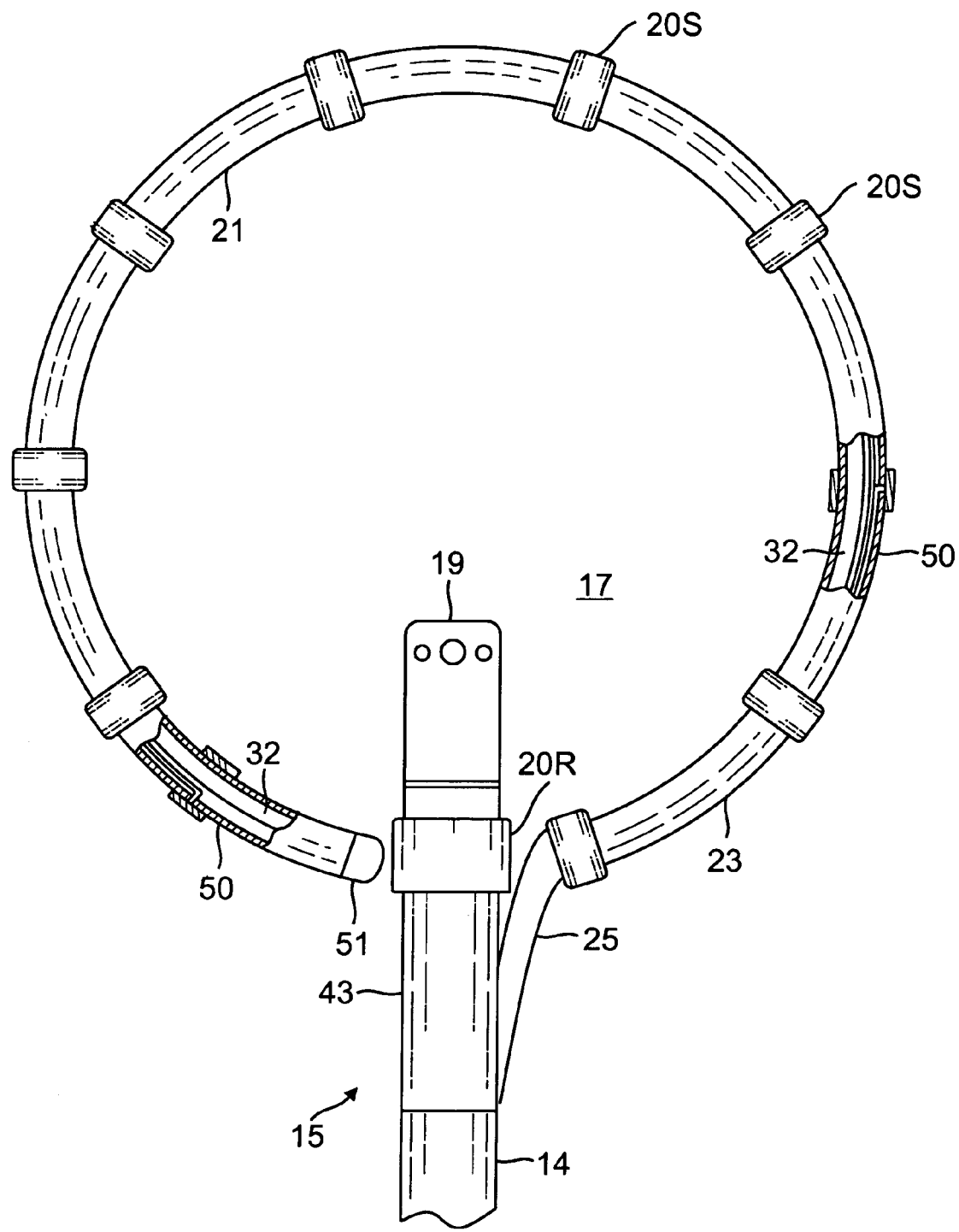
FIG. 5 is a top plan view of an embodiment of an electrode assembly including a tip section and a stabilizing member.

As illustrated in FIG. 5, the stabilizing member 21 is an open-ended, generally circular loop or halo that has a generally circular main portion 23 extending distally around the ablation electrode 19, and a generally straight portion 25 that extends from the connective tubing 43. As such, the distal tip 15 and the stabilizing member 21 are directly connected to each other so that the electrode assembly 17 is less likely to flip over or roll away from the selected epicardial treatment site.

The segment 25 is off-set from the connective tubing 43 at a small angle (e.g., less than about 45 degrees) where the connective tubing 43 and the tip electrode 19 lie along a diameter of the generally circular main segment 23 with the segment 23 extending distally around the tip electrode 19. The exposed length of the segment 25 ranges between about 70 mm and 78 mm, preferably between about 73 mm and 76 mm, and more preferably between about 75 mm and 76 mm, but can vary as desired. The segment 23 has a length ranging between about 70 mm and 75 mm, preferably between about 73 mm and 75 mm, and more preferably between about 72 mm and 73 mm, but can vary as desired.

Advantageously, the segments 23 and 25 of the stabilizing member 21 are coplanar with the tip electrode 19 such that all three lie with a plane to provide a flat profile. And because the puller wires 36 and their lumens 26 and 27 in the tubing 13 of the intermediate deflectable section 14 also lie generally in this plane, the stabilizing member 21 adopts a laterally sweeping motion during the bi-directional deflection of the tip section 15 and intermediate section 14.

The stabilizing member 21 with its segments 23 and 25 comprises a non-conductive covering or tubing 50 (shown partially broken away in FIG. 5) that spans the length of the segments 23 and 25. The covering or tubing 50 can be made of any suitable material that is flexible and biocompatible and preferably plastic, such as polyurethane or PEBAX. The tubing 50 (as with all tubes or tubing herein) may have any cross-sectional shape and may have a single lumen or multiple lumens. The illustrated embodiment, the tubing 50 has a single lumen that is occupied by the lead wires 30S or other electrical connections for ring electrodes 20S or any other electrical or electromagnetic elements that may be mounted on the stabilizing member 21. The lumen is also occupied by the support element 32 that can have shape memory or be preformed with the generally straight and generally circular shapes of the segments 23 and 25. A shape memory element can be straightened or bent out of its original shape upon exertion of a force and is capable of substantially returning to its original shape upon removal of the force. A suitable material for the shape memory element is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability.

As mentioned, the generally circular segment 23 is open-ended with a free distal end 51. This allows the stabilizing member 21 to be elongated with the distal end 51 distal of the tip electrode 20R so that the stabilizing member 21 can be more easily passed through an introducer and/or a dilator for entry into a patient's body. Once outside of the introducer or dilator, the stabilizing member 21 readily adopts its preformed shape, as understood by one of ordinary skill in the art. The end 51 is sealed with a dome of polyurethane glue or the like. A short ring, made of metal or plastic, and preferably polyimide, is mounted within the distal end of the non-conductive cover 50. The short ring prevents the distal end of the non-conductive cover 50 from collapsing, there by maintaining the diameter of the non-conductive cover at its distal end.

Figure 6A:
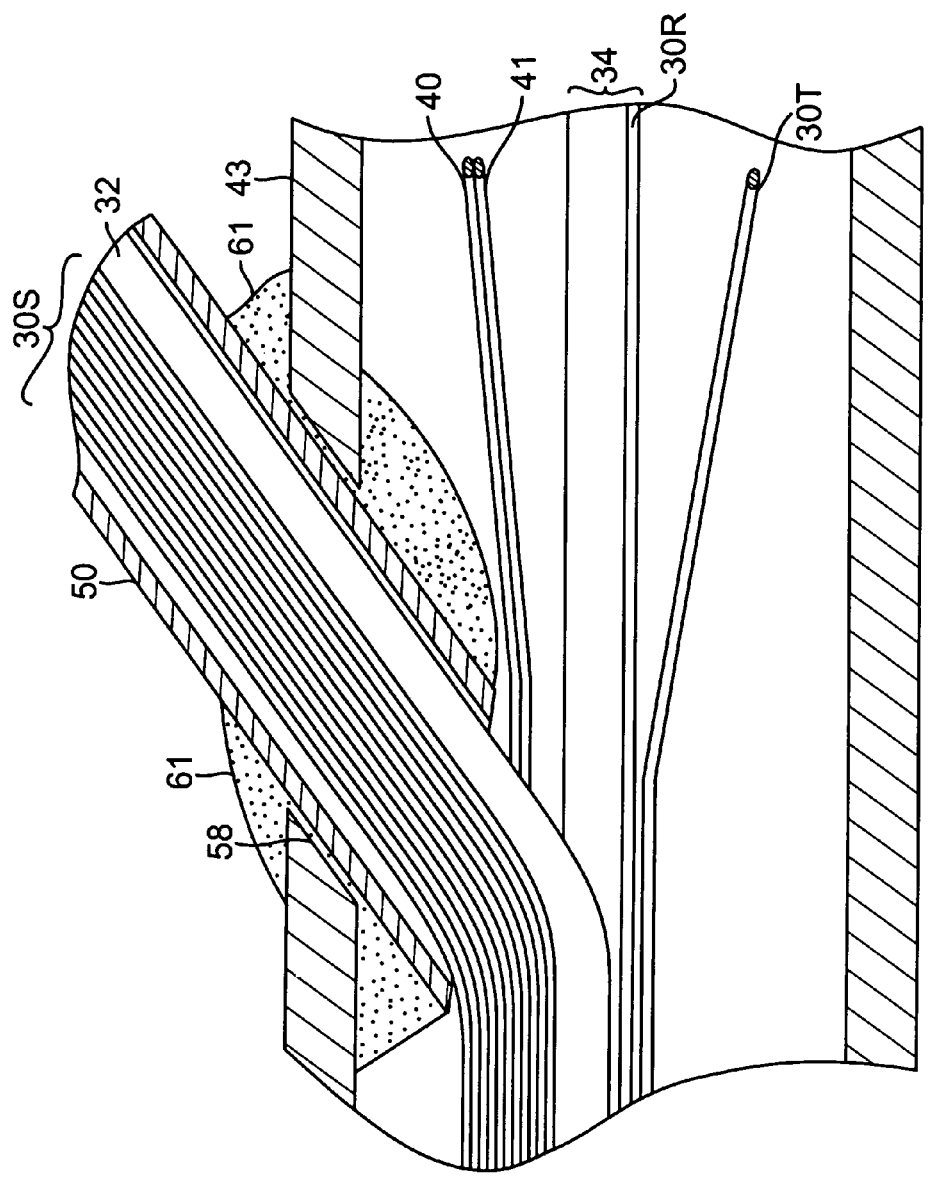
FIG. 6a is a side cross-sectional view of an embodiment of a connective tubing between the intermediate section and the tip section, showing a proximal end of the stabilizing member.

A means for attaching the tubing 50 of the stabilizing member 21 to the connective tubing 43 is shown in FIG. 6a. An opening 58 is cut or otherwise formed in the wall of the connective tubing 43 to receive a proximal end of the tubing 50 which is inserted into the opening to a depth of approx. 1 mm and affixed by glue 61 which also seals the opening 58. The lead wires 30S and the support member 32 for the stabilizing member 21 extending from the lumen 24 of the tubing 13 of the intermediate section 14 are received in the tubing 50 where they pass through the generally straight segment 25 and then the generally circular main segment 23, as needed. On the generally circular main segment 23, multiple ring electrode 20S are evenly spaced from each other and each is connected to a respective lead wire 30S as shown in FIG. 5. As mentioned, the proximal end of the member 32 is anchored near a proximal end of the lumen 24 of the intermediate section 14 (FIG. 2b).

Figure 6B:
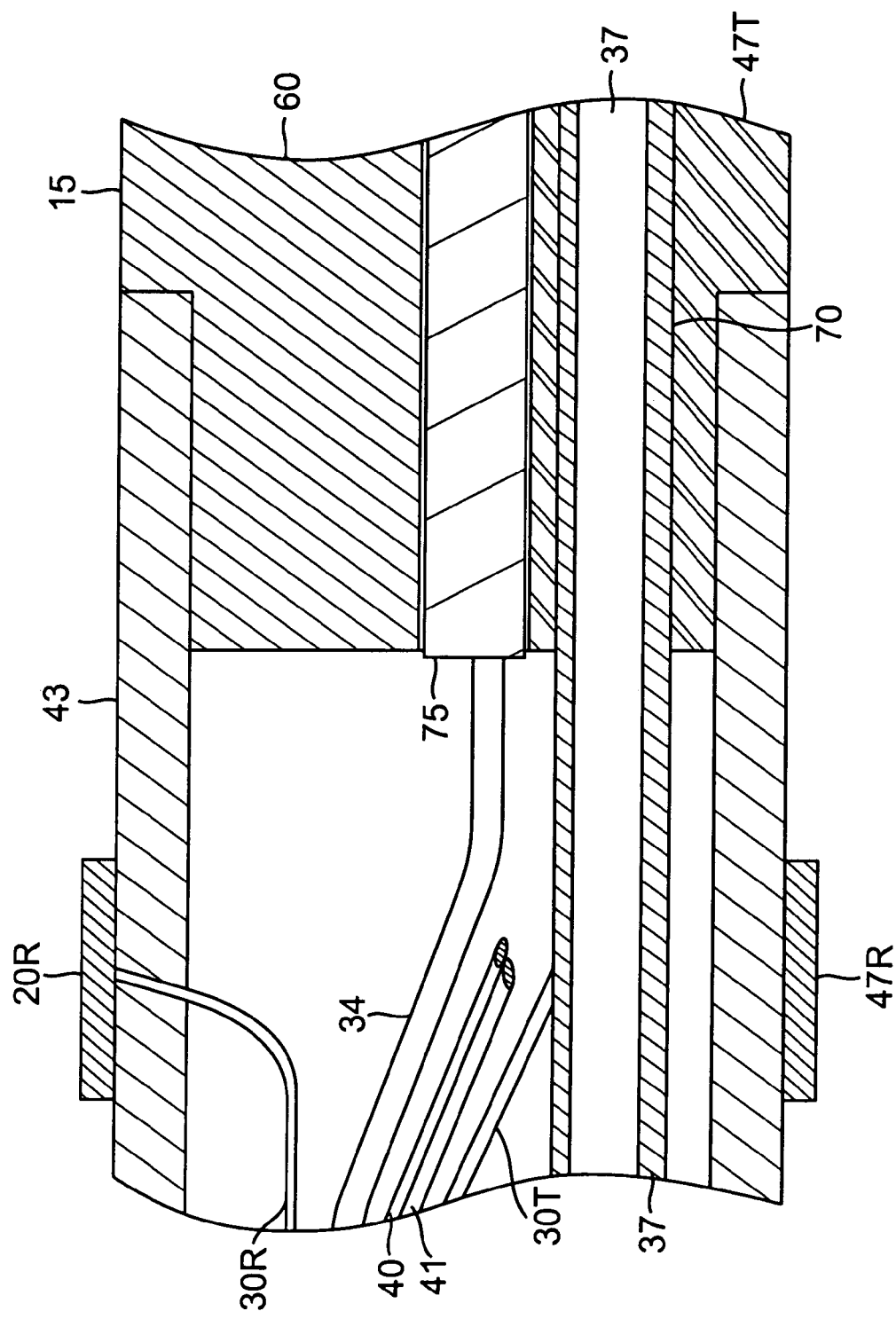
FIG. 6b is a side cross-sectional view of a junction between the connective tubing and the tip section of FIG. 1.

With reference to FIG. 6b, ring electrode 20R is mounted on the connective tubing 43 distal of the attachment location of the stabilizing member 21. The ring electrode is connected to the lead wire 30R that extends from the lumen 24 of the tubing 13 of the intermediate section 14.

Figure 7A:
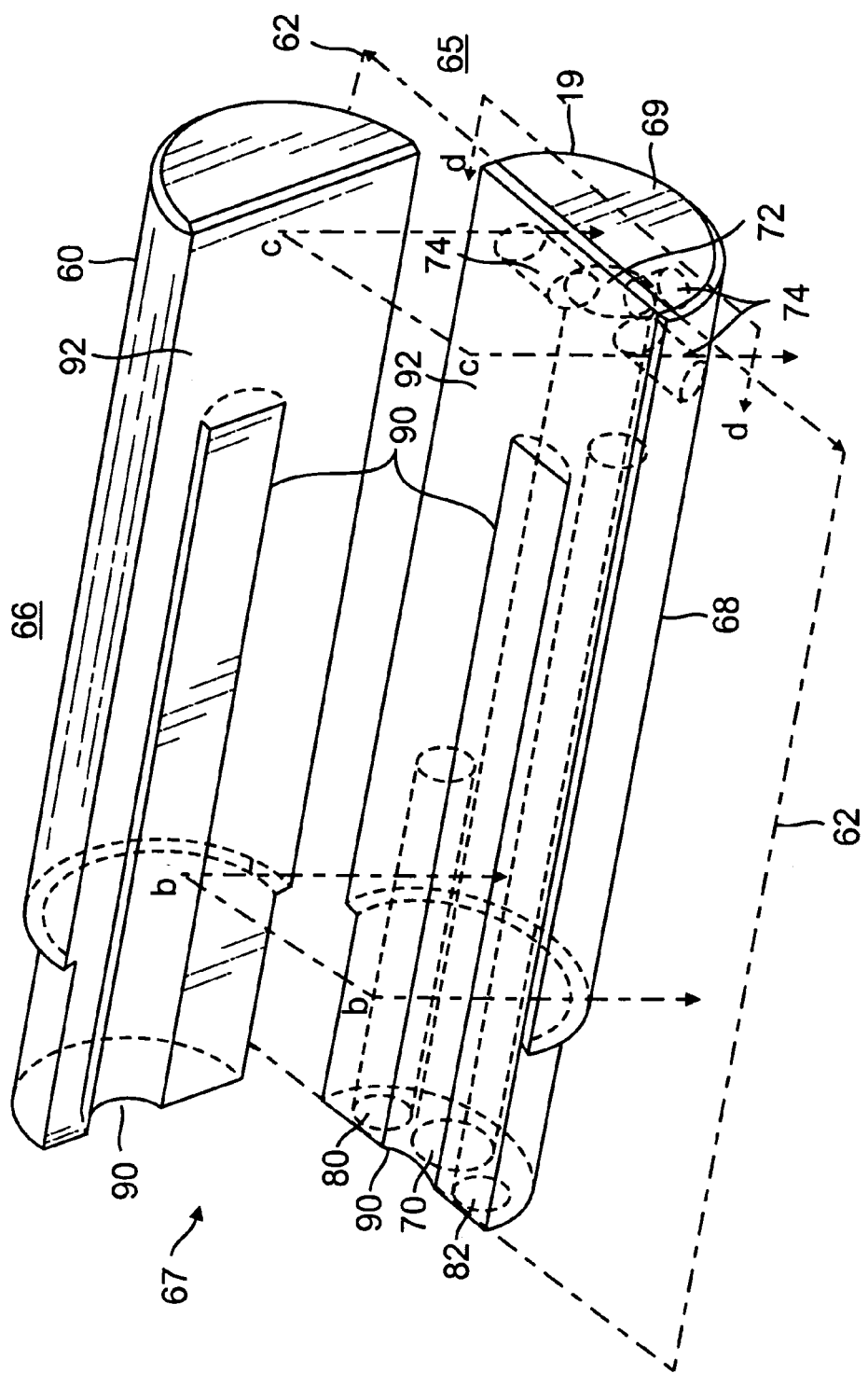
FIG. 7a is an exploded perspective view of an embodiment of a distal tip, including an ablation electrode and an insulation member.

As for the distal tip 15 shown in FIG. 7a, it has a generally monolithic cylindrical construction 65 with a distal end and a trepanned proximal end that is received in a distal end of the connective tubing 43. The cylindrical construction 65 is formed from the ablation electrode 19 and an insulation member 60 that thermally and electrically shields tissue from the ablation electrode. The insulation member effectively renders the ablation electrode 19 directional so that only an exposed side of the electrode 19 can contact tissue.

Figure 7C:
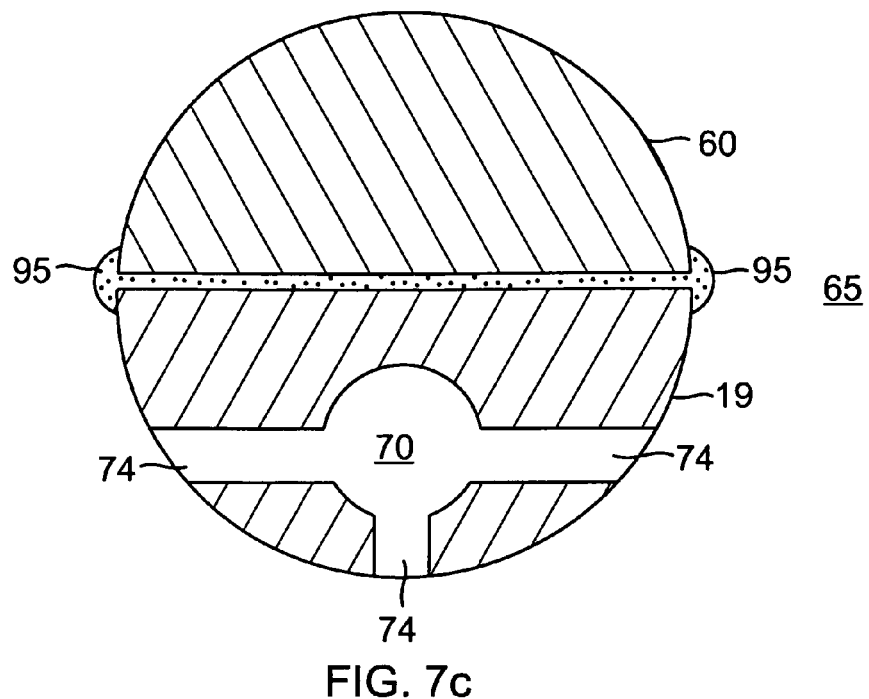
FIG. 7c is a longitudinal view of the distal tip of FIG. 7a, taken along line c-c.
Figure 7B:
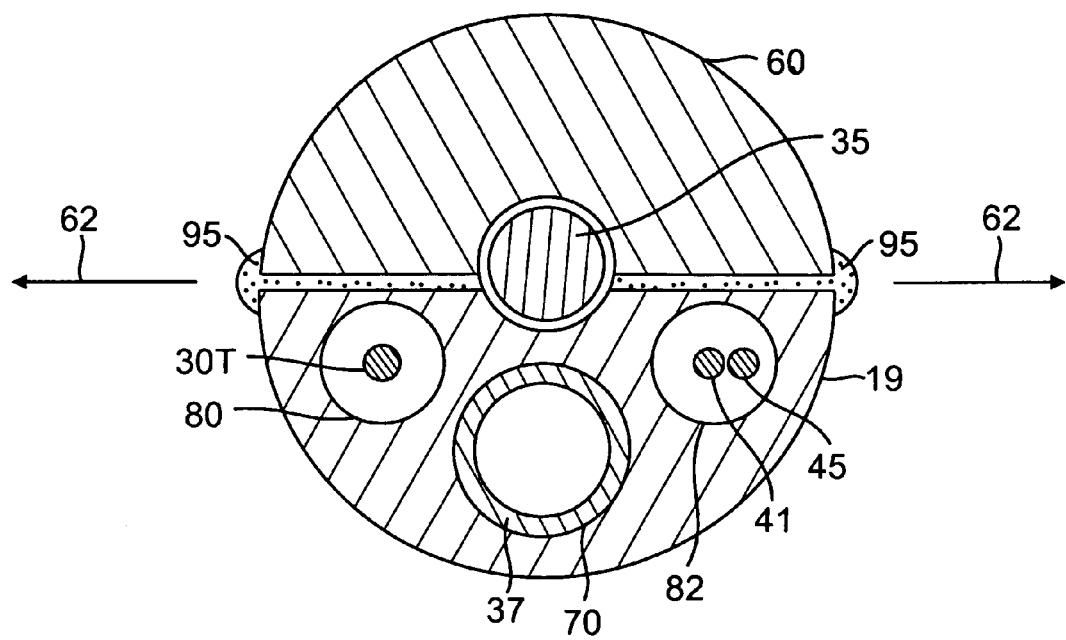
FIG. 7b is a longitudinal view of the distal tip of FIG. 7a, taken along line b-b.

With reference to the embodiments of FIGS. 7a-7c, the ablation electrode 19 and the insulation member 60 are generally two longitudinal halves or counterparts joined along a longitudinal axis of the cylindrical form 65. Advantageously, a plane of division 62 between the ablation electrode 19 and the insulation member 60 coincides with the plane of the stabilizing member 21 as well as the bi-directional deflection of the electrode assembly 17 as enabled by the intermediate section 14. Thus, the electrode assembly 17 effectively has the ablation electrode 19 exposed on one side of the stabilizing member 21 and the insulation member 60 exposed on an opposite side of the stabilizing member 21, wherein the electrode assembly 17 remains in this orientation as it is swept side to side during bi-directional deflection. And, where an operator has maneuvered the electrode assembly 17 so that the ablation electrode 19 is facing the epicardium and the insulation member 60 is facing the pericardium, the stabilizing member 21 tends to maintain that orientation while the electrode assembly is stationary or is deflected to sweep from side to side.

Various formations are provided in the ablation tip electrode 19, as further illustrated in FIG. 8. An elongated passage 70 for the irrigation tubing 37 is formed along the length of the electrode 19 an opening a proximal face of the electrode 19. At a distal end 72 of the passage 70, a multiple of branches 74 allow communication between the distal end 72 and outside of the tip electrode 19. In the illustrated embodiment, there are three generally perpendicular branches 74. A second elongated blind hole 80 is formed along the length of the electrode 19 for lead wire 30T for energizing the ablation tip electrode 19. A third elongated blind hole 82 is formed along the length of the electrode 19 for the thermocouple wires 40 and 41 for sensing the tip temperature. Between interfacing surfaces 92 of the electrode 19 and the insulation member 60, another blind hole 90 is effectively formed along the longitudinal axis for the electromagnetic position sensor 75. A coating of glue and/or other suitable adhesives 95 is used to join the interfacing surfaces 92.

The ring electrodes 20S and 20R are electrically connected to an appropriate mapping or monitoring system (not shown) by lead wires 30S and 30R. The distal tip electrode 19 is electrically connected to a source of ablation energy (not shown) by the lead wire 30T. Each electrode lead wire has its proximal end terminating in a connector at the proximal end of the control handle 16. More distally, the electrode lead wires extend through the central lumen 18 in the catheter body 12, and through the lumen 24 of the intermediate section 14. The portion of the lead wires extending through the central lumen 18 of the catheter body 12, and proximal end of the lumen 24 can be enclosed within a protective sheath (not shown), which can be made of any suitable material, preferably polyimide. The protective sheath is anchored at its distal end to the proximal end of the intermediate section 14 by gluing it in the lumen 24 with polyurethane glue or the like.

Each lead wire is attached to its corresponding ring electrode by any suitable method. A preferred method for attaching a lead wire to a ring electrode involves first making a small hole through the wall of the non-conductive covering or tubing. Such a hole can be created, for example, by inserting a needle through the non-conductive covering sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire around the non-conductive covering a number of times and stripping the lead wire of its own insulated coating on its outwardly facing surfaces.

The electrodes can be made of any suitable solid conductive material, such as platinum or gold, preferably a combination of platinum and iridium. The ring electrodes can be mounted onto the tubing with glue or the like. Alternatively, the ring electrodes can be formed by coating the tubing with an electrically conducting material, like platinum, gold and/or iridium. The coating can be applied using sputtering, ion beam deposition or an equivalent technique. While the disclosed embodiment uses bipolar ring electrodes on the stabilizing member 21 and a unipolar ring electrode on the connective tubing 43, it is understood that any number or combinations of uni- and bi-polar ring electrodes may be used as needed or appropriate.

The number of the ring electrodes on the assemblies can vary as desired. Preferably, the number of ring electrodes on the stabilizing member 21 ranges from about six to about twenty, preferably from about eight to about twelve, evenly spaced from each other. On the connective tubing 43, the number of ring electrodes ranges from about one to about four. In a disclosed embodiment, a distance of approximately 5 mm is provided between each ring electrode on the stabilizing member 21. Where the connective tubing 43 carries multiple ring electrodes, a distance of approximately 2 mm is desirable between each ring electrode.

The puller wires 36 are anchored at their proximal ends in the control handle 16. Separate and independent longitudinal movement of the deflection wire 36 relative to the catheter body 12, which results in, respectively, deflection of the intermediate section 14 and tip section 15 along plane 65, is accomplished by suitable manipulation of the control handle 16. A suitable control handle is disclosed in U.S. Pat. No. 7,377,906; issued May 27, 2008, entitled STEERING MECHANISM FOR BI-DIRECTIONAL CATHETER and in U.S. application Ser. No. 12/211,728, filed Sep. 16, 2008, entitled CATHETER WITH ADJUSTABLE DEFLECTION SENSITIVITY, the entire disclosures of which are hereby incorporated by reference.

Figure 9A:
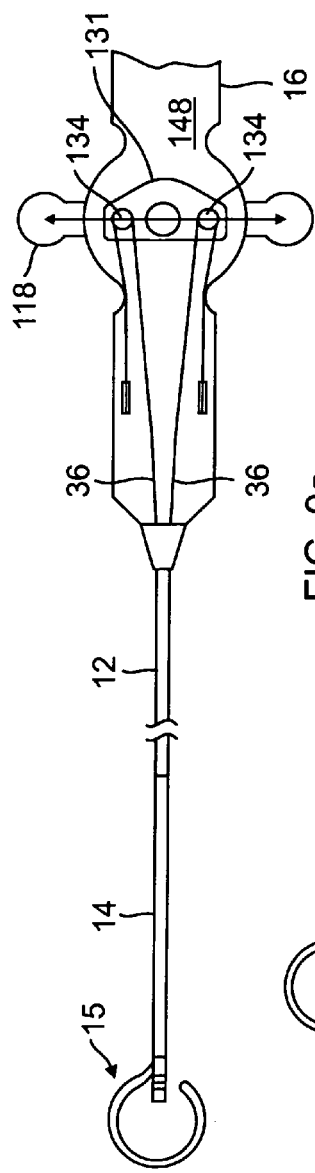
FIGS. 9a-9c illustrate bi-directional deflection of a catheter distal portion as controlled by manipulations of a control handle pursuant to an embodiment of a catheter of the present invention.
Figure 9B:
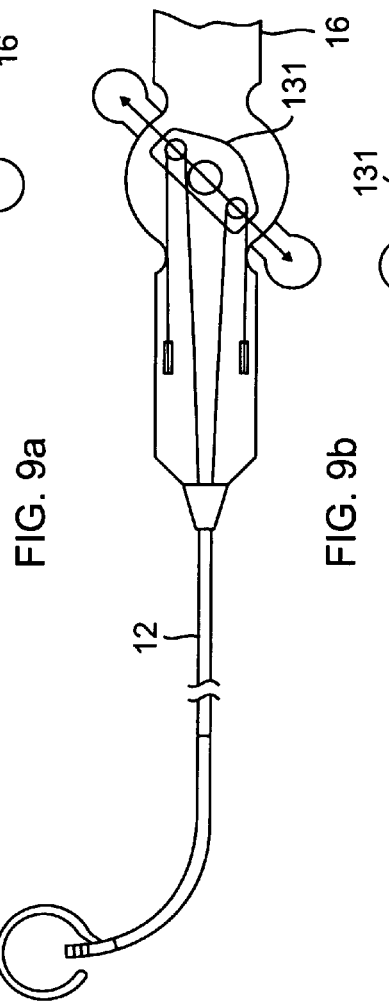
Figure 9C:
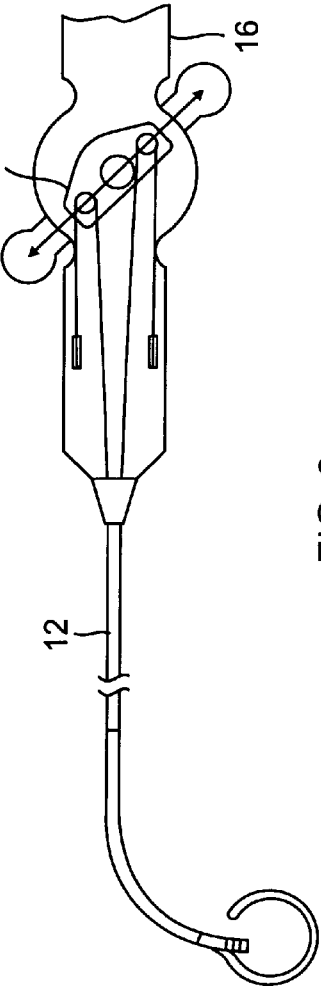

In the illustrated embodiment of FIGS. of 9a-9c, the control handle 16 has a deflection assembly 148 with a deflection arm 118, and a rotatable or rocker arm 131 supporting a pair of pulleys 134 that act on the puller wires 36 to deflect the intermediate section 14 and thus the tip section 15. The deflection arm 118 and the rocker arm 131 are rotationally aligned and coupled such that rotation of the deflection arm by a user rotates the pulley arm. As the rocker arm 131 is rotated by means of the deflection arm 118, the pulleys 134 are displaced from a neutral position (FIG. 9a) with one pulley drawing a puller wire 36 on one side of the catheter against its anchored proximal end for deflecting the section 14 toward that side (FIGS. 9b and 9c). By alternating the rotation of the deflection arm, the electrode assembly 17 sweeps side to side.

In use, a suitable guiding sheath is inserted into the patient with its distal end positioned in the pericardial sac using a subxiphoid approach. An example of a suitable guiding sheath for use in connection with the present invention is the Preface®. Braiding Guiding Sheath, commercially available from Biosense Webster, Inc. (Diamond Bar, Calif.). The stabilizing member 21 is straightened with its free end 51 distal of the tip electrode 19 so that the tip section 15 can readily enter and be fed through the guiding sheath. The catheter 10 is fed through the guiding sheath until the tip section 15 is at or near the tissue treatment site. The guiding sheath is pulled proximally, exposing the tip section 15 which allows the stabilizing member 21 to resume its generally circular shape and the intermediate section 14 as needed.

As shown in FIG. 3, the user orients the electrode assembly 17 so that the ablation electrode 19 faces the epicardium and the insulation member 60 faces the pericardium. The electrode assembly 17 is adapted to remain in this orientation since the stabilizing member 21 is effectively sandwiched between the epicardium and the pericardium. As the user manipulates the deflection arm 118 of the control handle, the electrode assembly 17 sweeps side to side over a surface area of the epicardial tissue with minimal risk of injury to surrounding tissue. In particular, the circular shape of the stabilizing member 21 is atraumatic and allows the tip section 15 to sweep in the pericardial sac without snagging tissue. Moreover, the predetermined bend in the intermediate section 14 toward the side of the ablation electrode 19 provides the curved or arched profile that ensures electrode contact with the epicardium. Additionally, the braided tubing 13 of the intermediate section 14 provides "back" support and a degree of rigidity to the catheter to further ensure tissue contact and minimize the risk of the electrode assembly 17 rolling or flipping out of position.

The ring electrodes 20S and 20R can be used for mapping and the tip electrode 19 for ablation by RF energy, or other types of energy including microwave and laser. The ring electrodes also permit measurement of the electrical activity surrounding the ablation site so that the catheter can provide real-time and continuous feedback of the potential recordings or electrograms (ECGs) of the epicardial tissue as ablation is performed. The insulation member 60 thermally and electrically insulates adjacent tissue, especially the pericardium, from ablation by providing a physical barrier.

Fluid, e.g., saline or heparin, can be transported to the ablation site from the tip electrode to cool tissue, reduce coagulation and/or facilitate the formation of deeper lesions. It is understood that other fluids can be delivered, as well, including any diagnostic and therapeutic fluids, such as neuroinhibitors and neuroexcitors for altering the state of ganglionated plexi.

Figure 10:
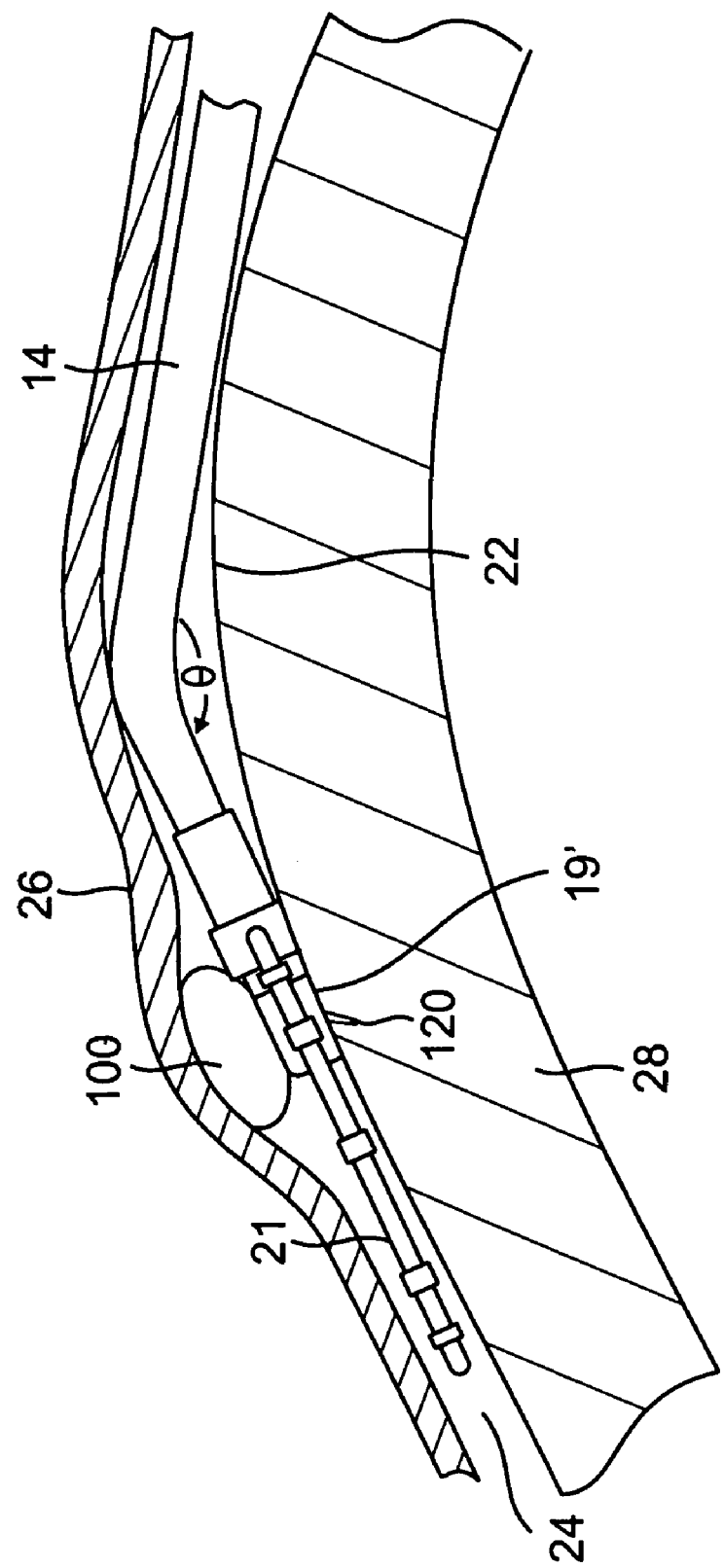
FIG. 10 is a side cross-sectional view of an alternate embodiment of a catheter of the present invention positioned in a pericardial cavity between the parietal pericardium and the epicardium of a heart, having an inflation member adapted to lift the pericardium from the distal tip.

In another embodiment, a tip section 15' includes an inflatable member, e.g., a balloon 100, that thermally and electrically insulates a directional tip electrode 19' from contact with adjacent and opposing tissue, including pericardial tissue. As illustrated in FIG. 10, the balloon 100 when inflated lifts the pericardium 26 away from the electrode assembly 19'. As discussed below, there are similarities as well as differences between the tip section 15' and the aforementioned tip section 15.

With reference to the embodiment of FIGS. 11a-11b, the tip section 15' includes an insulation member 60' that together with the ablation electrode 19' forms a generally elongated cylindrical form 65'. The cylindrical form 65' has an atraumatic distal end 66', and a trepanned proximal end 67' that is received in the distal end of a connective tubing 43'. In the illustrated embodiment, an elongated passage 70' is formed in the ablation electrode 19' for an irrigation tubing 37'. At a distal end 72' of the passage 70', a multiple of branches 74' allow communication between the distal end 72' and outside of the tip electrode 19'. Elongated blind holes 80' and 82' alongside the passage 70' are formed for lead wire 30T' and thermocouple wires 40' and 41', respectively. An electromagnetic sensor 75' however is housed in the connective tubing 43' (FIG. 14) so as to leave more space in the tip section 15'. Glue and/or other suitable adhesives 195 is used in a recess 112 formed in the ablation electrode 19' to join the electrode 19' and the insulation member 60'. Additionally, a latch in the form of an insert 114 and a recess 116 (FIG. 11b) is formed at a distal end 66' of the tip section 15 so the electrode 19' and the insulation member 60' remain secured to each other.

Figure 12:
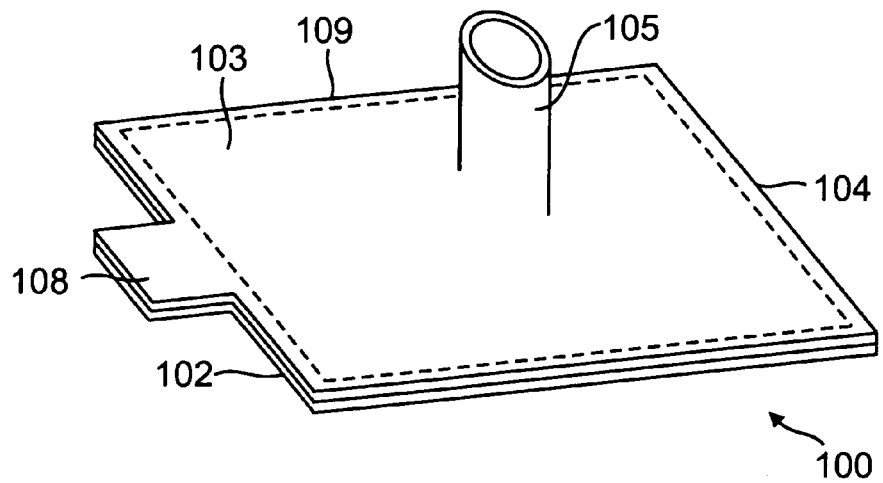
FIG. 12 is a perspective view of an embodiment of an inflation member in accordance with a feature of the present invention.

As shown in the embodiment of FIG. 12, the balloon 100 of the tip section 15' has a generally rectangular shape and is of a two-ply construction with a top panel 102 and a bottom panel 103 that are joined to each other around peripheral edges, including end edges 104 and longitudinal edges 109, to form a fluid-tight seal. The top panel 102 and bottom panel 103 are made of a suitable highly elastic and biocompatible material such as polyisopreme. The bottom panel 103 is configured with an inlet port 105 suitable for mounting over a distal end of an inflation tube 106 through which fluid is delivered into and out of the balloon by means of a pump (not shown) from a source (not shown) through the control handle 16. Suitable fluids for inflating the balloon include air and saline. It is understood that the fluid can also be a fluid whose temperature is suitable for cooling the surrounding pericardial tissue.

The balloon 100 is affixed to an outer surface 110 of the insulation member 60' by means of a coating of glue or adhesive 115 between the surface 110 and the bottom panel 103 of the balloon. The balloon also has a distal portion 108 which is received in a recess or pocket 109 which is filled with glue 111 or the like to secure the distal edge of the balloon to the insulation member 60'. This safety feature prevents the distal edge of the balloon from detaching from the tip section 15'. Moreover, the longitudinal edges 109 of the panels 102 and 103 of the balloon 100 are tucked inwardly and secured by glue or adhesive along side edges 113 between the ablation electrode 19' and the insulation member 60'. An elongated passage 116 is formed in the ablation electrode 19' for the inflation tubing 106 that feeds into the balloon 100. At a distal end of the passage 116, a transverse passage 117 is formed to receive the inlet port 105 of the balloon.

Figure 13C:
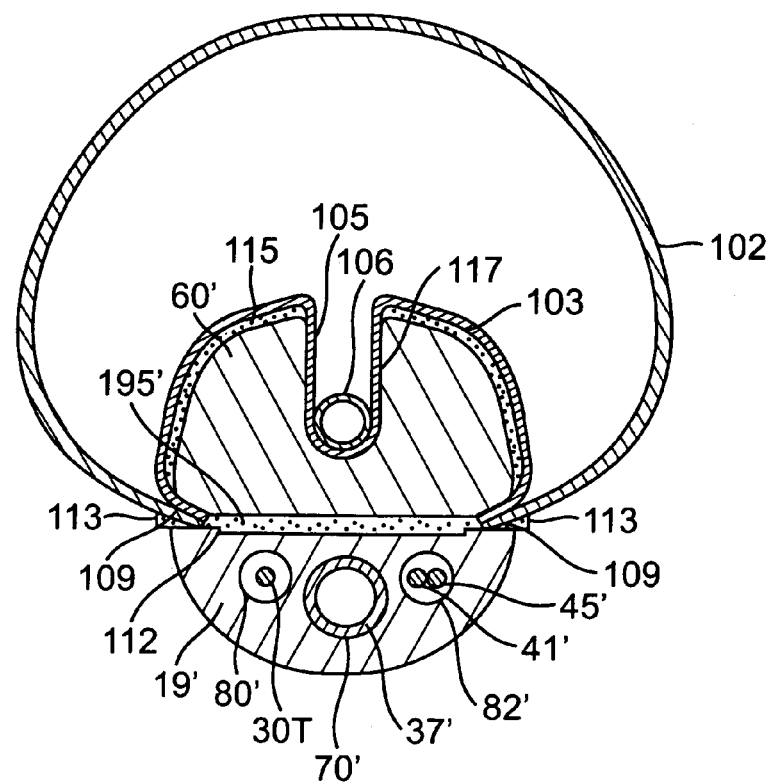
FIG. 13c is a longitudinal cross-sectional view of the distal tip of FIG. 13, taken along line c-c.
Figure 13:
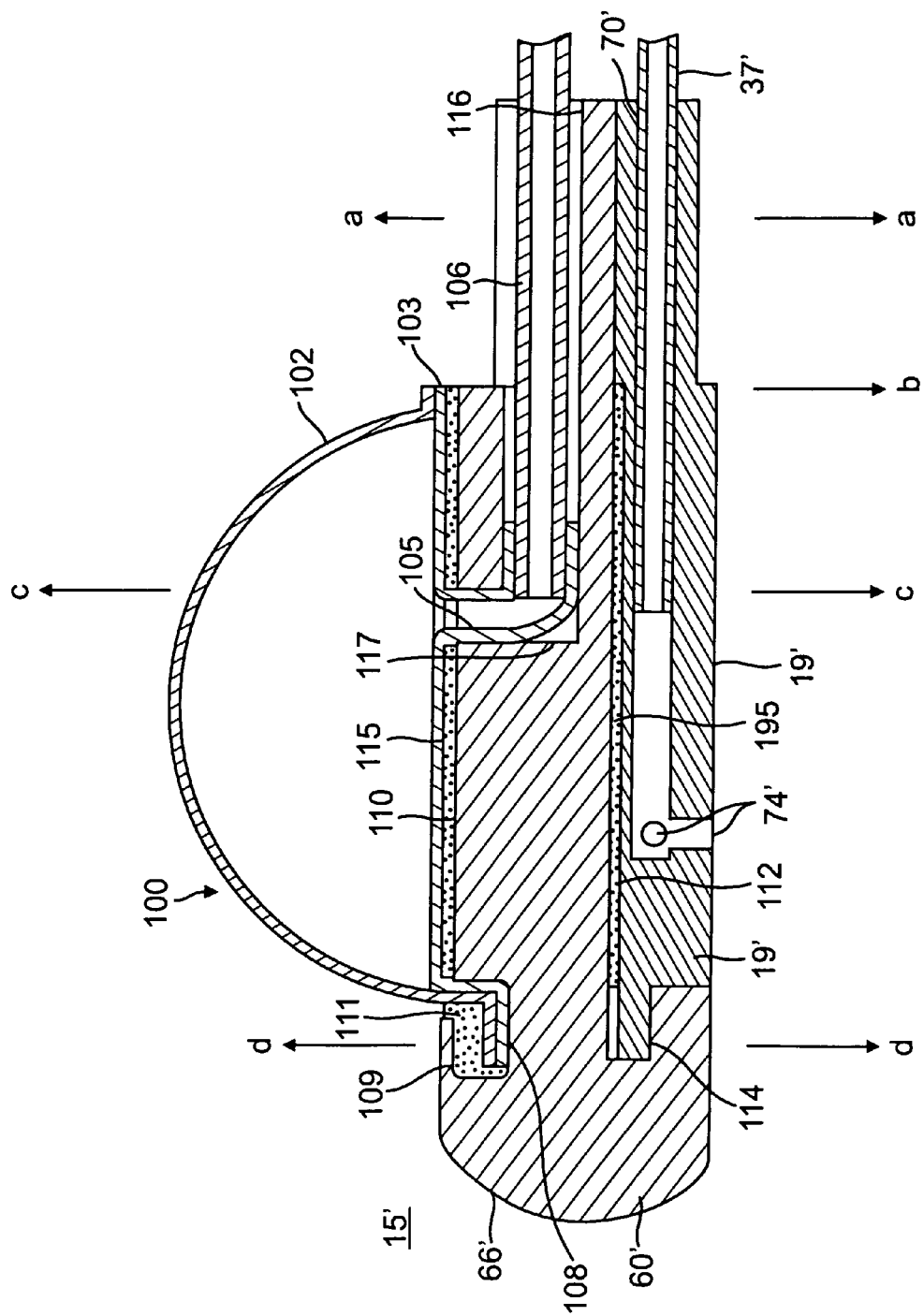
FIG. 13 is a side cross-sectional view of the distal tip of FIGS. 11a and 11b, with its the inflation member inflated.
Figure 13A:
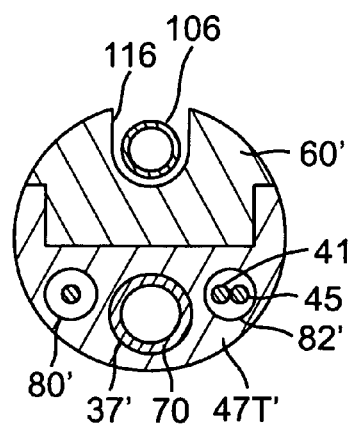
FIG. 13a is a longitudinal cross-sectional view of the distal tip of FIG. 13, taken along line a-a.
Figure 13B:
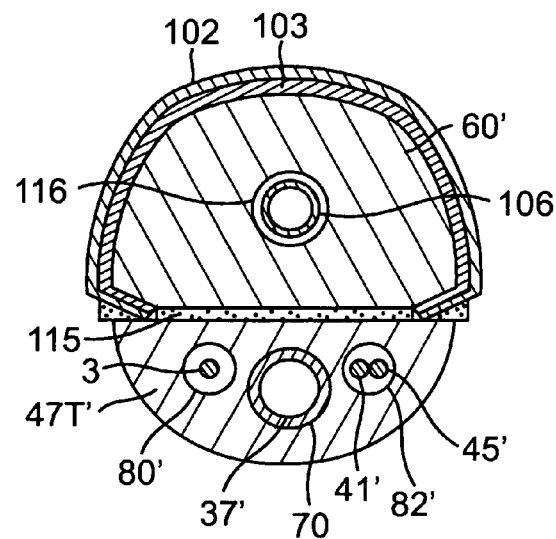
FIG. 13b is a longitudinal cross-sectional view of the distal tip of FIG. 13, taken along line b-b.
Figure 13D:
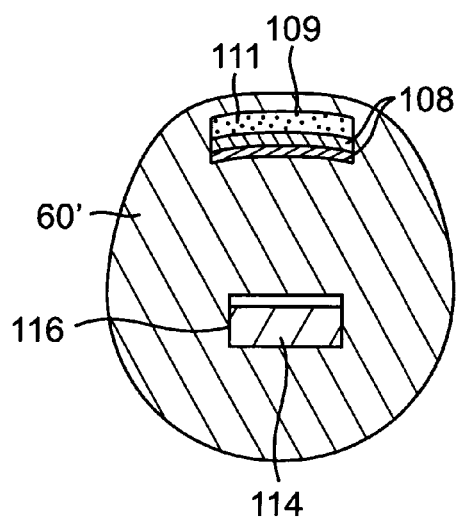
FIG. 13d is a longitudinal cross-sectional view of the distal tip of FIG. 13, taken along line d-d.

In the disclosed embodiment, the balloon 100, and in particular, the top panel 102 is constructed so that when the balloon is inflated the top panel expands into a generally spherical shape that expands significantly above the ablation electrode 19' as well as to the sides (FIG. 13c) so that tissue above and to the sides of the ablation electrode is lifted away.

It is understood that the balloon 100 in an alternate embodiment need not include a bottom panel 103. That is, the top panel 102 alone can form a fluid tight seal along its peripheral edges with the outer surface 110 of the insulation member 60,' and the inflation tubing 106 can be sealed to the distal end of the passage 116 to effectively deliver fluid into and out of the balloon for inflation and deflation.

Figure 14:
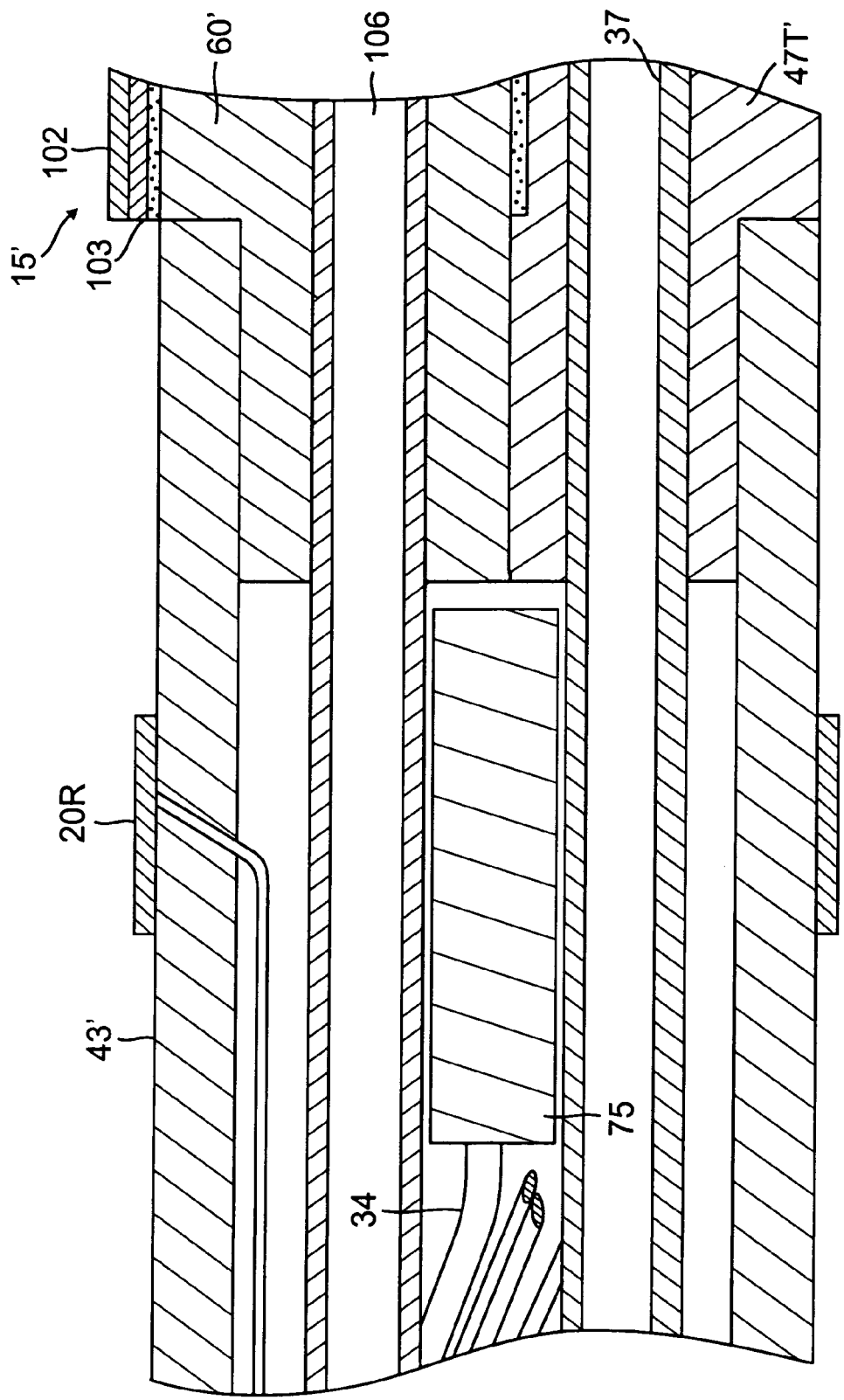
FIG. 14 is a side cross-sectional view of an embodiment of a connective tubing adapted for use with a distal tip of FIG. 13.
Figure 15:
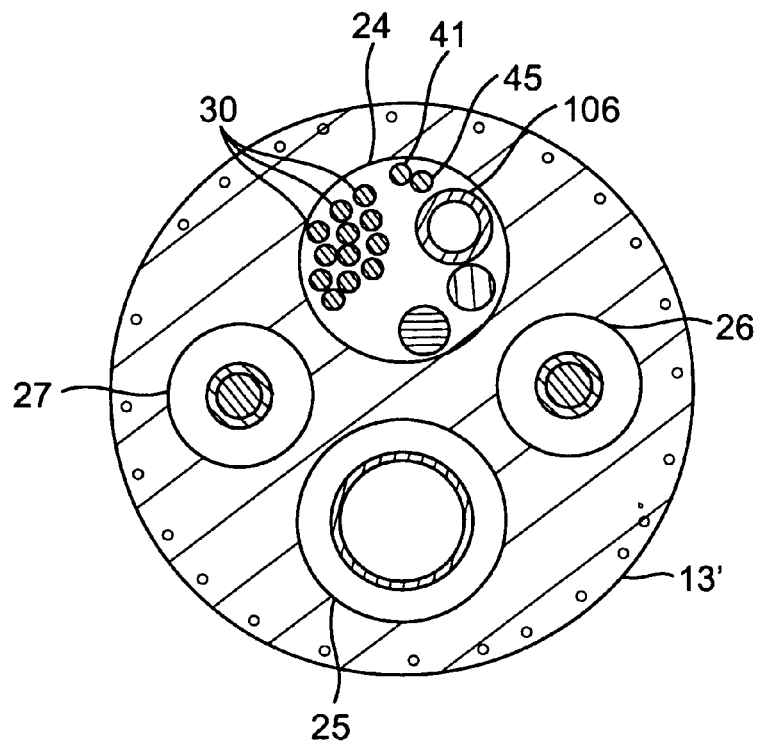
FIG. 15 is a longitudinal cross-sectional view of an embodiment of an intermediate section adapted for use with the distal tip of FIG. 13.

Regardless of the structure of the balloon, the inflation tubing 106 extends proximally through a connective tubing 43' connecting the electrode assembly 17' and the intermediate section 14 as shown in FIG. 14. The inflation tubing 106 extends proximally through a first lumen 24' of a tubing 13' of the intermediate section.

Figure 19:
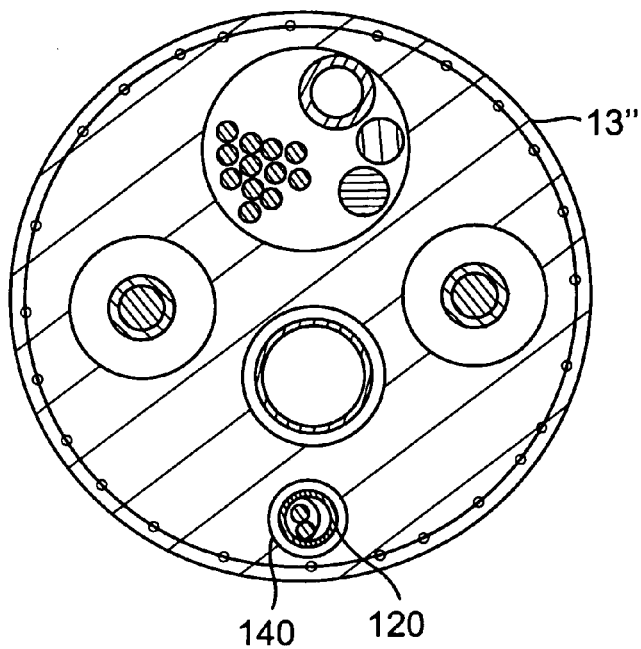
FIG. 19 is a longitudinal cross-sectional view of an embodiment of an intermediate section suitable for use with the distal tip of FIGS. 16a and 16b.
Figure 18A:
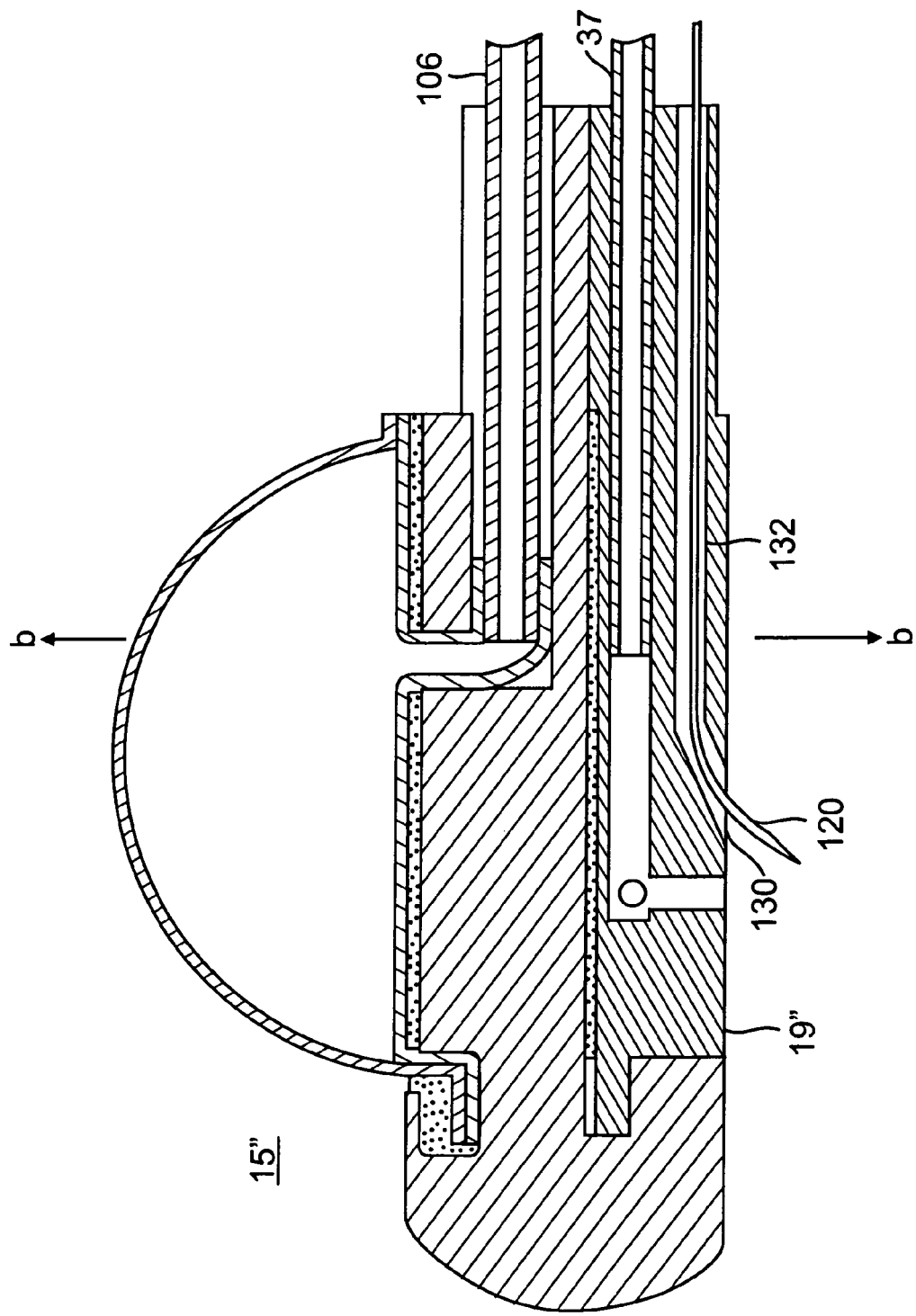
FIG. 18a is a side cross-sectional view of the distal tip of FIG. 16a showing an inflated inflation member and a deployed injection needle in accordance with a feature of the present invention.
Figure 18B:
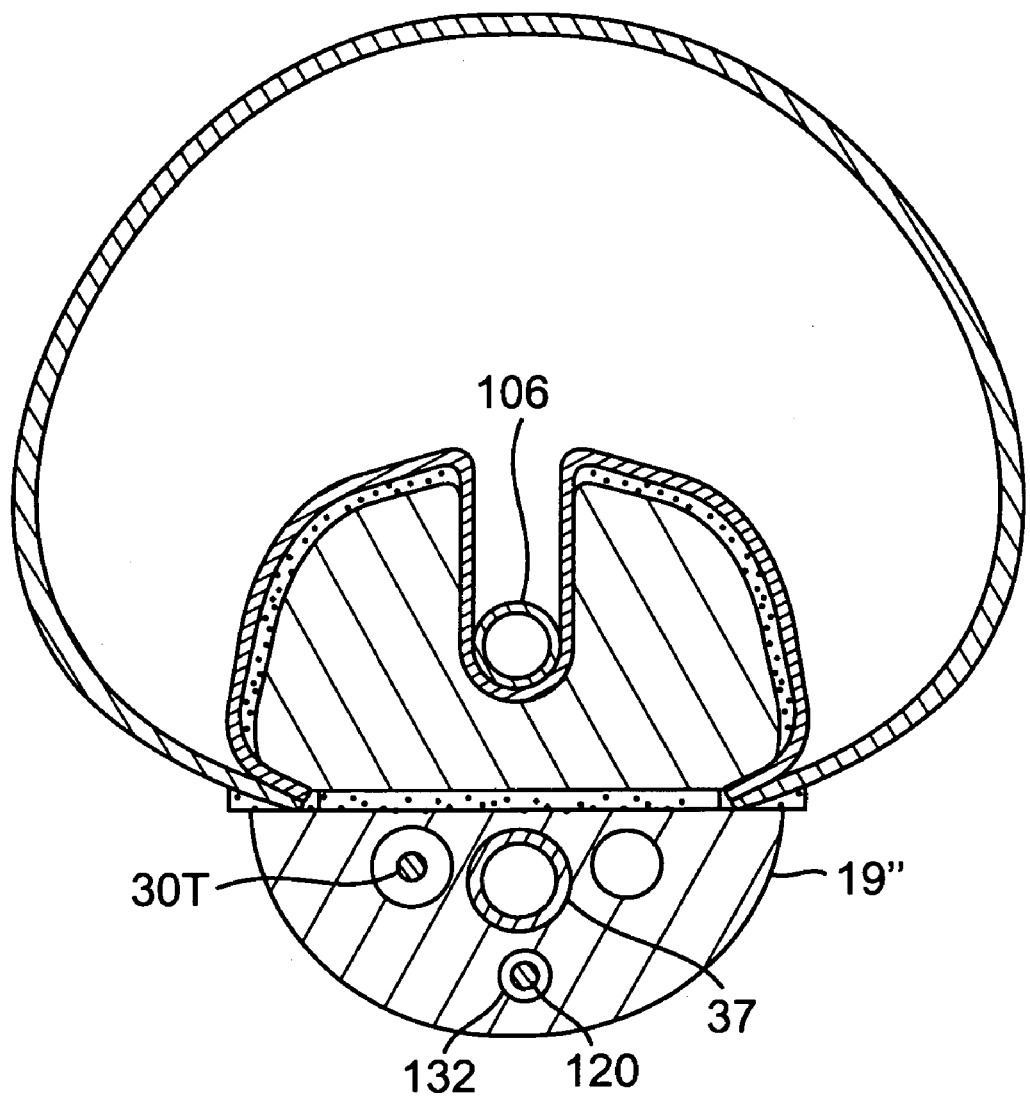
FIG. 18b is a longitudinal cross-sectional view of the distal tip of FIG. 18a, taken along line b-b.
Figure 20:
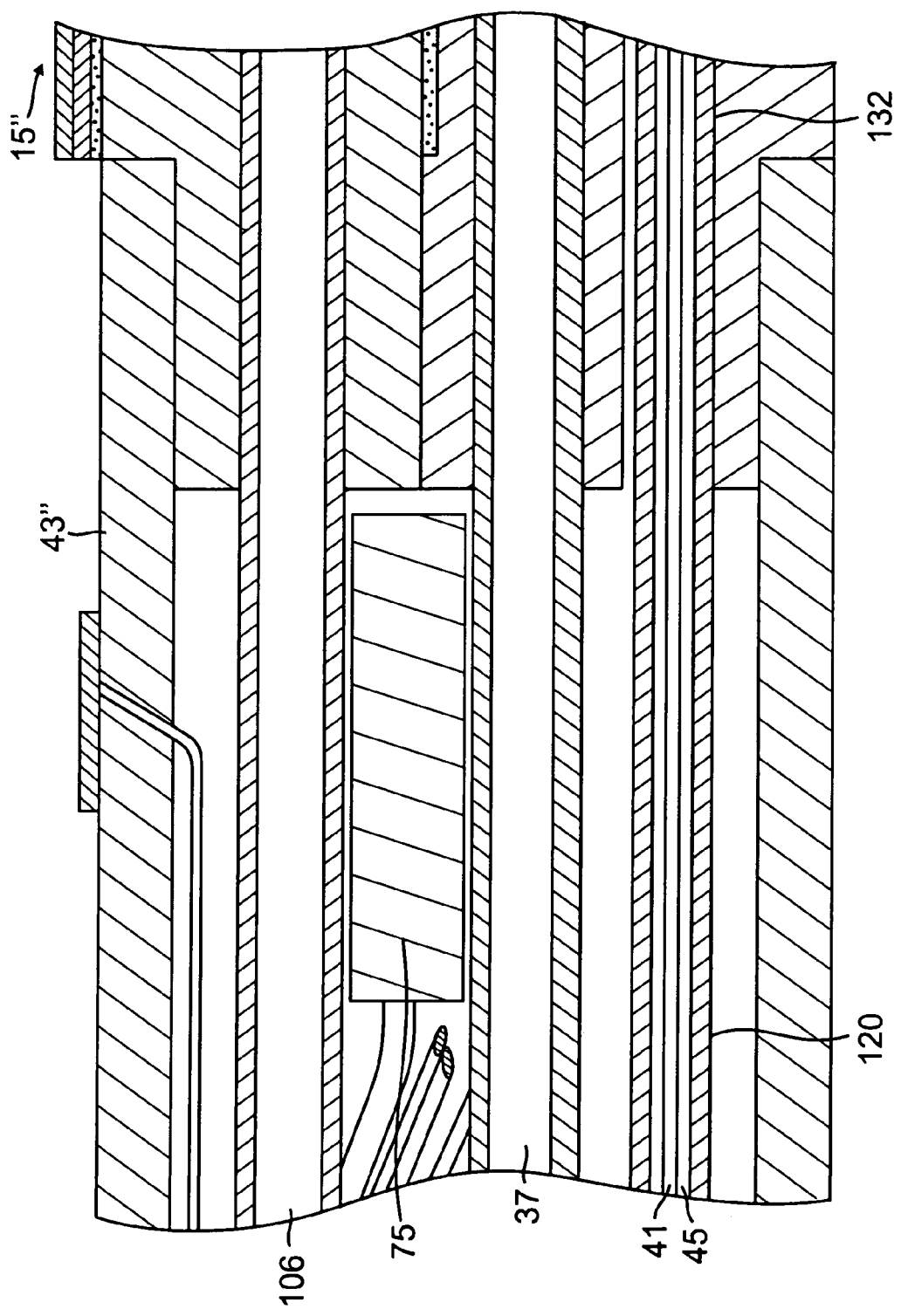

In yet another embodiment, an injection needle 120 is adapted to extend from an opening 130 for an elongated passage 132 formed in a tip ablation electrode 19". The injection needle 120 includes a tapered distal end (FIG. 18a) that is adapted to puncture tissue and deliver agents passed through a lumen 134 extending through the injection needle (FIG. 17). Inside the lumen 134 are thermocouple wires 41 and 45 whose distal ends are affixed near the distal end of the needle for measuring temperature of the tissue into which the needle is inserted. The wires 41 and 45 are secured at their distal ends to an interior wall of the lumen by glue or adhesives 136. As shown in FIG. 19, the injection needle 120 extends proximally through the connective tubing 43 and a fifth lumen 140 in a tubing 13" of the intermediate section.

The injection needle 120 is made of any suitably rigid material, including plastic or metal, including stainless steel and nitinol. The material may also have shape-memory such that a distal portion of the needle has a preshaped curvature to provide angulation of the needle in puncturing tissue below the electrode assembly (see FIG. 18a).

It is also contemplated that any of the aforementioned tip sections 15, 15', 15" can be constructed wholly or in part(s) with magnetic material to incorporate Remote Magnetic Technology (RMT). For example, any of the tip electrodes and/or the insulation members can be made of magnetic material or carry magnetic members so that the catheter can be magnetically navigated by an operator from a remote locate. Such a catheter is described in U.S. patent application Ser. No. 12/125,903, filed May 22, 2008, entitled MAGNETICALLY GUIDED CATHETER WITH CONCENTRIC NEEDLE PORT, the entire disclosure of which is hereby incorporated by reference.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter adapted for use in a cavity between epicardial and pericardial tissue of a heart, comprising:
    an elongated catheter body;
    an electrode assembly distal the catheter body, the electrode assembly including a tip section and a loop member, the tip section including an ablation electrode on one side and an insulation member on an opposite side, the loop member extending generally around the tip section in generally a same plane as the tip section;
    an intermediate section extending between the catheter body and the electrode assembly, the intermediate section adapted for deflecting the loop member and the tip section bi-directionally generally within the plane of the loop member and the tip section.

2. A catheter of claim 1, wherein the ablation electrode is adapted to ablate the epicardial tissue, and the insulation member is adapted to insulate the pericardial tissue from the ablation electrode.

3. A catheter of claim 2, wherein the tip section further includes an inflatable member.

4. A catheter of claim 3, further comprising an inflation tubing whose distal end is received in the tip section, the inflation tubing adapted to deliver fluid to and from the inflatable member.

5. A catheter of claim 2, wherein the tip section is of a generally cylindrical form with a longitudinal axis, and the ablation electrode and the insulation member are affixed to each other along the longitudinal axis.

6. A catheter of claim 5, wherein each of the ablation electrode and the insulation member has a generally semi-circular cross section.

7. A catheter of claim 5, further comprising an irrigation tubing whose distal end is received in a passage formed in the tip section, the irrigation tubing adapted to deliver fluid to pass through the passage.

8. A catheter of claim 1, wherein the loop member has shape memory to assume a predetermined configuration that extends distally around the tip section.

9. A catheter of claim 8, wherein the predetermined configuration is generally a circle.

10. A catheter of claim 1, wherein the loop member is open ended.

11. A catheter of claim 1, wherein the intermediate section is configured with a predetermined angle.

12. A catheter of claim 1, wherein the tip section contains magnetic material responsive to remote magnetic navigation of the tip section.

13. A catheter of claim 1, further comprising an injection needle whose distal end is received in a passage formed in the tip section, the injection needle being adapted to extend outside of the tip section to puncture tissue.

14. A catheter of claim 13, further comprising thermocouple wires extending through the needle.

15. A catheter of claim 1, wherein the loop member carries ring electrodes.

16. A catheter of claim 1, wherein the loop member has a generally straight portion and a generally circular portion, both of which lie in the plane of the loop member and tip section.

17. A catheter of claim 1, wherein the inflatable member is mounted on an outer surface of the insulation member.

18. A catheter of claim 1, further comprising puller wires extending through the catheter body and the intermediate section to enable the bi-directional deflection.

19. A catheter of claim 18, further comprising a control handle proximal the catheter body, proximal ends of the puller wires being anchored in the control handle, wherein the control handle is configured for a user to manipulate the puller wires.

* * * * *